United States Patent
Svenstrup et al.

(10) Patent No.: US 10,513,524 B2
(45) Date of Patent: Dec. 24, 2019

(54) PDE9 INHIBITORS WITH IMIDAZO TRIAZINONE BACKBONE AND IMIDAZO PYRAZINONE BACKBONE FOR TREATMENT OF PERIPHERAL DISEASES

(71) Applicant: H. LUNDBECK A/S, Valby (DK)

(72) Inventors: Niels Svenstrup, København V (DK); Kate Wen, Shanghai (CN); Yazhou Wang, Shanghai (CN)

(73) Assignee: H. LUNDBECK A/S (DK)

( * ) Notice: Subject to any disclaimer, the term of this patent is extended or adjusted under 35 U.S.C. 154(b) by 0 days.

(21) Appl. No.: 15/742,086

(22) PCT Filed: Jul. 6, 2016

(86) PCT No.: PCT/EP2016/065964
§ 371 (c)(1),
(2) Date: Jan. 5, 2018

(87) PCT Pub. No.: WO2017/005786
PCT Pub. Date: Jan. 12, 2017

(65) Prior Publication Data
US 2018/0194770 A1    Jul. 12, 2018

(30) Foreign Application Priority Data

Jul. 7, 2015  (DK) ................................. 2015 00393
Jul. 10, 2015 (DK) ................................. 2015 00407
Apr. 7, 2016  (DK) ................................. 2016 00209

(51) Int. Cl.
| C07D 487/04 | (2006.01) |
| A61P 7/00 | (2006.01) |
| A61P 13/08 | (2006.01) |

(52) U.S. Cl.
CPC ............ *C07D 487/04* (2013.01); *A61P 7/00* (2018.01); *A61P 13/08* (2018.01)

(58) Field of Classification Search
CPC .................................................. C07D 487/04
USPC ....................................................... 514/250
See application file for complete search history.

(56) References Cited

U.S. PATENT DOCUMENTS

| 6,362,178 | B1 | 3/2002 | Niewohner et al. |
| 7,709,468 | B2 | 5/2010 | Calderwood et al. |
| 7,741,324 | B2 | 6/2010 | Crew et al. |
| 8,299,080 | B2 | 10/2012 | Okada et al. |
| 8,563,565 | B2 | 10/2013 | Norimine et al. |
| 9,434,731 | B2 | 9/2016 | Siegel et al. |
| 9,434,733 | B2 | 9/2016 | Svenstrup et al. |
| 9,533,992 | B2 | 1/2017 | Svenstrup et al. |
| 9,725,453 | B2 | 8/2017 | Bursavich et al. |
| 9,850,249 | B2 | 12/2017 | Svenstrup et al. |
| 2004/0020186 | A1 | 2/2004 | Orlando et al. |
| 2004/0220186 | A1 | 11/2004 | Bell et al. |
| 2011/0082147 | A1 | 4/2011 | Harbeson et al. |
| 2012/0157458 | A1 | 6/2012 | Ripka et al. |
| 2012/0295925 | A1 | 11/2012 | Tung et al. |
| 2015/0045348 | A1 | 2/2015 | Svenstrup et al. |

FOREIGN PATENT DOCUMENTS

| CA | 2296224 A1 | 7/2000 |
| CN | 1344268 A | 4/2002 |
| CN | 101448829 A | 6/2009 |
| CN | 101557826 A | 10/2009 |
| CN | 101687876 B | 12/2012 |
| CN | 103313988 B | 6/2016 |
| EP | 2123301 A1 | 11/2009 |
| EP | 2123801 A1 | 11/2009 |
| WO | WO-9924433 A1 | 5/1999 |
| WO | WO-03037432 A1 | 5/2003 |
| WO | WO-03037899 A1 | 5/2003 |
| WO | WO-03093270 A1 | 11/2003 |
| WO | WO-2004096811 A1 | 11/2004 |
| WO | WO-2005041972 A1 | 5/2005 |
| WO | WO-2007137819 A1 | 12/2007 |
| WO | WO-2008139293 A1 | 11/2008 |
| WO | WO-2010084438 A1 | 7/2010 |
| WO | WO-2011028820 A1 | 3/2011 |
| WO | WO-2012040230 A1 | 3/2012 |
| WO | WO-2012110441 A1 | 8/2012 |
| WO | 2013/053690 A1 | 4/2013 |
| WO | 2013/110768 A1 | 8/2013 |

OTHER PUBLICATIONS

Conran, N. "Prospects for early investigational therapies for sickle cell disease" (2015) Expert Opin. Investig. Drugs 24(5):595-602.
Almedia, C. B. et al., "Hydroxyurea and a cGMP-amplifying agent have immediate benefits on acute vaso-occlusive events in sickle cell disease mice" (2012) Blood 120(14):2879-2888.
Ückert, S. et al., "Phosphodiesterase (PDE) inhibitors in the treatment of lower urinary tract dysfunction" (2011) Br. J. Clin. Pharmacol 72(2): 197-204.
International Search Report and Written Opinion dated Aug. 11, 2016 in application No. PCT/EP2016/065964, entitled, "PDE9 Inhibitors With Imidazo Triazinone Backbone and Imidazo Pyrazinone Backbone for Treatment of Peripheral Diseases".
Berge, S.M. et al., (1977) "Pharmaceuticals Salts", J. Pharma. Sci. 66: 1-19.
Blockland, A. et al., (2006) "Improving Memory: A Role for Phosphodiesterases", Curr. Pharm. Des. 12(20):2511-2523.
Breer, H. et al., (1990) "Rapid Kinetics of Second Messenger Formation in Olfactory Transduction" Nature 345 :6270):65-68.
Chawla, et al. Current Research & Information on Pharmaceutical Sciences (Crips), 5(1), 2004, 9-12.

(Continued)

*Primary Examiner* — Kahsay Habte
(74) *Attorney, Agent, or Firm* — Wilson Sonsini Goodrich & Rosati

(57) ABSTRACT

The present invention relates to PDE9 inhibitors and their use for treatment of benign prostate hyperplasia and sickle cell disease.

4 Claims, 3 Drawing Sheets

(56) References Cited

OTHER PUBLICATIONS

Cooke, S.F. et al., (2006) "Plasticity in the Human Central Nervous System" Brain 129(7):1659-1673.
Duncton, M.A.J. et al. (2008) "Preparation of Aryloxetances and Arylazetidines by Use of an Alkyl-Aryl Suzuki Coupling" Organic Letters 10(15):3259-3262.
Ex Parte Sauerberg, Appeal 2015-007064, Decided Jan. 12th, 2017.
Extended European Search Report dated Oct. 25, 2016 in Application No. 16185105.0, entitled PDE9I with Imidazo Pyrazinone Backbone.
Extended European Search Report dated Mar. 10, 2017 in European Application No. 17152165.1, entitled "PDE9I With Imidazo Triazinone Backbone".
Fisher, D.A. et al., (1998) "Isolation and Characterization of PDE9A, a Novel Human cGMP-specific Phosphodiesterase" J_Boil_Chem_ 273(25):15559-15564.
Hackam, et al., Translation of Research Evidence From Animals to Humans;JAMA, 296(14), 2006, 1731-1732.
International Search Report and Written Opinion PCT EP2012/069936 (Wo 2013/053690) (2012)(9 pages).
International Search Report and Written Opinion PCT EP2013/051451 (WO 2013/110768) (2013)(11 pages).
Mehats, C. et al., (2002) "Cyclic Nucleotide Phosphodiesterases and their Role in Endocrine Cell Signaling" Trends in Endocrinol. & Metab. 13:29-35.
Jordan, V. C., "Tamoxifen: a most unlikely pioneering medicine" Nature Reviews: Drug Discovery, 2, 2003, 205.
International Search Report and Written Opinion dated Sep. 13, 2012 in International Application No. PCT/CN2012/070718 filed Jan. 26, 2012.
van der Staay, J.F. et al. (2008) "The Novel Selective PDE9 Inhibitor Bay 73/6691 Improved Learning and Memory in Rodents" Neuropharma 55(5):908-918.
Verhoest et al., 2009, "Identification of a Brain Penetrant PDE9A Inhibitor Utilizing Prospective Design and chemical Enablement as a Rapic Lead Optimization Strategy", Journal of Medicinal Chemistry, vol. 52, No. 24, pp. 7946-7949.
Wunder, F. et al., (2005) "Charachertization of the First Potent and Selective PDE9 Inhibitor Using a cGMP Reporter sell Line" Mol. Pharmacol_ 68(6):1775-1781.
Zhou, M. et al., (1994) "Role of Guanylyl Cyclase and cGMP-dependent Protein Kinase in Long-Term Potentiation" Nature 36(6472):635-639.

PDE9 INHIBITORS WITH IMIDAZO TRIAZINONE BACKBONE AND IMIDAZO PYRAZINONE BACKBONE FOR TREATMENT OF PERIPHERAL DISEASES

CROSS REFERENCE TO RELATED APPLICATIONS

This application is a 35 U.S.C. § 371 U.S. National Stage Entry of International Application No. PCT/EP216/065964 filed Jul. 6, 2016, entitled, PDE9 INHIBITORS WITH IMIDAZO TRIAZINONE BACKBONE AND IMIDAZO PYRAZINONE BACKBONE FOR TREATMENT OF PERIPHERAL DISEASES, which claims the benefit of priority of DK Provisional Patent Application No. PA201500393, filed Jul. 7, 2015, entitled PDE9INHIBITORS WITH IMIDAZO TRIAZINONE BACKBONE AND IMIDAZO PYRAZINONE BACKBONE FOR TREATMENT OF PERIPHERAL DISEASES, DK Provisional Patent Application No. PA201500407, filed Jul. 10, 2015, entitled PDE9 INHIBITORS WITH IMIDAZO TRIAZINONE BACKBONE AND IMIDAZO PYRAZINONE BACKBONE FOR TREATMENT OF PERIPHERAL DISEASES, and DK Provisional Patent Application No. PA201600209, filed Apr. 7, 2016, entitled PDE9 INHIBITORS WITH IMIDAZO TRIAZINONE BACKBONE AND IMIDAZO PYRAZINONE BACKBONE FOR TREATMENT OF PERIPHERAL DISEASES, the contents of each of which are herein incorporated by reference in their entirety.

FIELD OF THE INVENTION

The present invention relates to cyclic guanylate monophosphate (cGMP)-specific phosphodiesterase type 9 inhibitors (hereinafter referred to as PDE9 inhibitors) of the form 3H-imidazo[5,1-f][1,2,4]triazin-4-ones or 7H-imidazo[1,5-a]pyrazin-8-ones and their use as a medicament for treatment of peripheral diseases. Moreover the invention relates to a pharmaceutical composition comprising 3H-imidazo[5,1-f][1,2,4]triazin-4-ones and 7H-imidazo[1,5-a]pyrazin-8-ones.

BACKGROUND OF THE INVENTION

Phosphodiesterases (PDEs) are a family of enzymes degrading cyclic nucleotides and thereby regulating the cellular levels of second messengers throughout the entire body. PDEs represent attractive drug targets, as proven by a number of compounds that have been introduced to clinical testing and the market, respectively. PDEs are encoded by 21 genes that are functionally separated into 11 families differing with respect to kinetic properties, substrate selectivity, expression, localization pattern, activation, regulation factors and inhibitor sensitivity. The function of PDEs is the degradation of the cyclic nucleotide monophosphates cyclic Adenosine MonoPhosphate (cAMP) and/or Guanosine MonoPhosphate (cGMP), which are important intracellular mediators involved in numerous vital processes including the control of neurotransmission and smooth muscle contraction and relaxation.

PDE9 is cGMP specific (Km cAMP is >1000× for cGMP) and is hypothesized to be a key player in regulating cGMP levels as it has the lowest Km among the PDEs for this nucleotide. PDE9 is expressed throughout the brain at low levels with the potential for regulating basal cGMP.

In the periphery, PDE9 expression peaks in prostate, intestine, kidney and haematopoietic cells opening for the therapeutic potential in various peripheral indications.

Benign prostate hyperplasia (BPH) is one of the most prevalent conditions in the aging male population and represents a major health problem (Ueckert S et al., Expert Rev Clin Pharmacol. 2013 May; 6(3):323-32). BPH results in the formation of large nodules in the periurethral region of the prostate, which could lead to urinary tract obstruction. BPH is predominantly the result of a stromal proliferative process, and a significant component of prostatic enlargement results from smooth-muscle proliferation. The current pharmacological treatment of BPH includes al adrenergic blockers, 5-α-reductase inhibitors and more recently the PDE5 inhibitor tadalafil. PDE5 inhibitors are known to mediate smooth muscle relaxation via increased cGMP levels. The cGMP specific PDE9 is expressed at high levels in the prostate and PDE9 inhibition may thus offer potential antiproliferative benefits for BPH.

PDE9 is widely distributed in the urothelial epithelium of human lower urinary tract and PDE9 inhibition may be beneficial in lower urinary tract dysfunctional epithelium (LUDE) disease (Nagasaki et al., BJU Int. 2012 March; 109(6):934-40). Dysfunctional lower urinary tract epithelium can affect the bladder, urethra, labia or vaginal introitus in women, and the prostatic ducts and urethra in men (Parsons L C et al., 2002).

PDE9 expression has been shown in murine corpus cavernosum and chronic PDE9 inhibition was demonstrated to result in amplified NO-cGMP mediated cavernosal responses and thereby opening for potential benefit in erectile dysfunction (DaSilva et al., Int J Impot Res. 2013 March-April; 25(2):69-73). Currently approved treatment for erectile dysfunction is the class of PDE5 inhibitors, increasing cGMP in the smooth muscle cells lining the blood vessels supplying the corpus cavernosum of the penis.

cGMP PDE inhibition has been shown to enhance muscle microvascular blood flow and glucose uptake response to insulin (Genders et al., Am J Physiol Endocrinol Metab. 2011 August; 301(2):E342-50). The targeting of cGMP specific PDE9, which is expressed in muscle and blood vessels may provide a promising avenue for enhancing muscle insulin sensitivity and thereby be beneficial for the treatment of type 2 diabetes.

PDE9 inhibition may represent a novel and first line treatment for Sickle Cell Disease (SCD), a genetic disorder leading to vaso-occlusive processes responsible for much of the mortality in SCD patients. SCD disease results from a point mutation in the hemoglobin (HBB) gene producing abnormal sickle hemoglobin (HbS), which polymerizes and creates rigid and sticky sickled red blood cells. Sickled red blood cells result in chronic inflammation, elevated cell adhesion, oxidative stress, endothelial dysfunction culminating in vaso-occlusive processes.

There is to date no cure for SCD. Treatment options include blood transfusion and treatment with the anti-cancer agent hydroxyurea. Blood transfusions correct anemia by increasing the number of normal, non-sickled red blood cells in circulation. Regular transfusion therapy can help prevent recurring strokes in children at high risk. Hydroxyurea has been approved for the treatment of SCD and shown to reduce the frequency of painful crisis and hospitalization. The mechanism by which hydroxyurea is hypothesized to ameliorate the symptoms of SCD is two-fold; a) increase in non-sickled fetal hemoglobin production and b) decrease in cell adhesion. Specifically, hydroxyurea a) increases fetal non-sickled haemoglobin production via cGMP signalling, which has been shown to result in increased red blood cell survival and b) increases nitric oxide and cGMP levels, thereby decreasing adhesion and increasing survival. In summary, the evidence to date supports the notion that that both mechanisms by which hydroxyurea promotes benefits in SCD are mediated via increased cGMP.

PDE9 is expressed specifically in the human haematopoietic system including neutrophils, reticulocytes erythroid and erythroleukaemic cells. Furthermore, SCD patients exhibit a marked and significant increase in PDE9 expression in reticulocytes and neutrophils (Almeida et al., Br J Haematol. 2008 September; 142(5):836-44). Evidence additionally demonstrates a link between PDE9 and cell adhesion since PDE9 inhibition results in the reversal of the increased adhesive properties of SCD neutrophils (Miguel et al., Inflamm Res. 2011 July; 60(7):633-42). The mechanism by which PDE9 inhibition decreases cell adhesion has been shown to be mediated via increased cGMP and decreased endothelial adhesion molecule expression. Importantly, in an animal model of SCD, the PDE9 inhibitor mediated decrease in cell adhesion had the functional effect of increased cell survival. In addition to demonstrating effects on decreased cell adhesion comparable to hydroxyurea, PDE9 inhibition results in increased fetal non-sickled haemoglobin production. Finally, Almeida and colleagues demonstrated that treatment with hydroxyurea combined with PDE9 inhibition in a mouse model of SCD leads to added benefit of PDE9 inhibitor in amplifying the cGMP elevating effects of hydroxyurea (Almeida et al., Blood. 2012 Oct. 4; 120(14):2879-88). In conclusion, PDE9 inhibition can modulate both the expression of fetal haemoglobin production as well as decrease cell adhesion, both mechanisms key for the treatment of SCD.

WO 2013/053690 discloses PDE9 inhibitors with imidazopyrazinone backbone for the use as a medicament, such as in the treatment of patients suffering from cognitive impairments, in particular cognitive impairments that relate to neurodegenerative diseases such as cortical dementia (e.g. Alzheimer's disease) or subcortical dementia, e.g. AIDS related dementia.

WO 2013/110768 discloses PDE9 inhibitors with imidazotriazinone backbone for the use as a medicament, such as in the treatment of patients suffering from cognitive impairments, in particular cognitive impairments that relate to neurodegenerative diseases such as cortical dementia (e.g. Alzheimer's disease) or subcortical dementia, e.g. AIDS related dementia.

WO 2012/040230 discloses PDE9 inhibitors with imidazotriazinone backbone for the use as a medicament in the treatment of PDE9 associated diseases, including CNS and neurodegenerative disorders.

WO 2008/139293 and WO 2010/084438 both disclose amino-heterocyclic compounds that are PDE9 inhibitors and their use in treating neurodegenerative and cognitive disorders.

SUMMARY OF THE INVENTION

There is a constant need for improved treatment of the peripheral diseases benign prostate hyperplasia (BPH), urinary tract dysfunctional epithelium disease, erectile dysfunction, type 2 diabetes and sickle cell disease (SCD) and for that purpose the use of PDE9 inhibitors may be very useful. Since PDE9 is expressed throughout the brain at with the potential basal cGMP and thus signalling cascades shown to regulate synaptic transmission, it is evidently important that PDE9 inhibitors for the treatment of peripheral diseases have a low blood brain barrier penetration (BBB penetration) to avoid potential centrally-mediated side effects.

The present invention provides novel PDE9 inhibitors that have been shown to have a low blood brain barrier penetration and thus may be particularly useful for the treatment of peripheral diseases such as benign prostate hyperplasia (BPH), urinary tract dysfunctional epithelium disease, erectile dysfunction, type 2 diabetes and sickle cell disease (SCD). Further, the PDE9 inhibitors of the present invention are significantly stronger PDE9 inhibitors than PDE1 inhibitors which is important as PDE1 is expressed in heart and testes and inhibition of these PDE1 isoforms is thought to be a potential cause of cardiovascular and reproductive side effects.

The following compounds are encompassed by the invention:

Compound (P1)

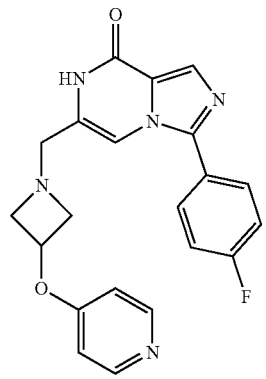

P1

Compound (P2)

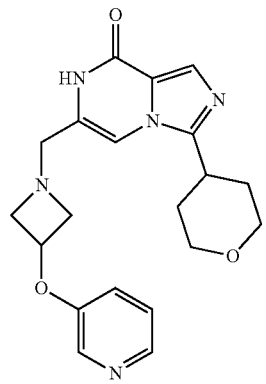

P2

Compound (P3)

P3 (racemate)

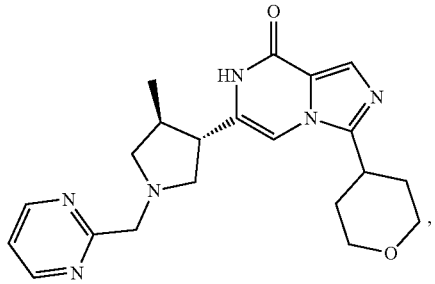

racemate and enantiomerically pure variants of compound P3.

Compound (P4)

A further aspect of the invention is directed to synthesis of P1, P2, P3 and P4. A still further aspect of the invention is directed to the enantioselective synthesis of compound P3 comprising the conversion of the intermediate compound rac-35 to (S,S)-35.

DETAILED DESCRIPTION OF THE INVENTION

Embodiments of the Invention

Figure 1:
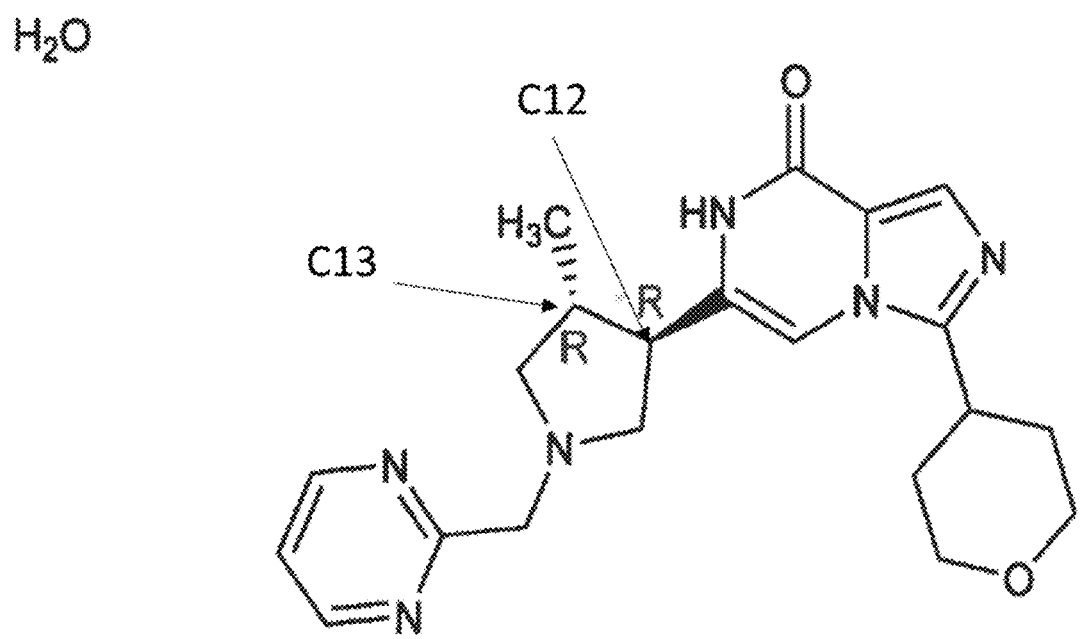
FIG. 1 shows the absolute stereochemistry of Compound P3 enantiomer 2 monohydrate.
Figure 2A:
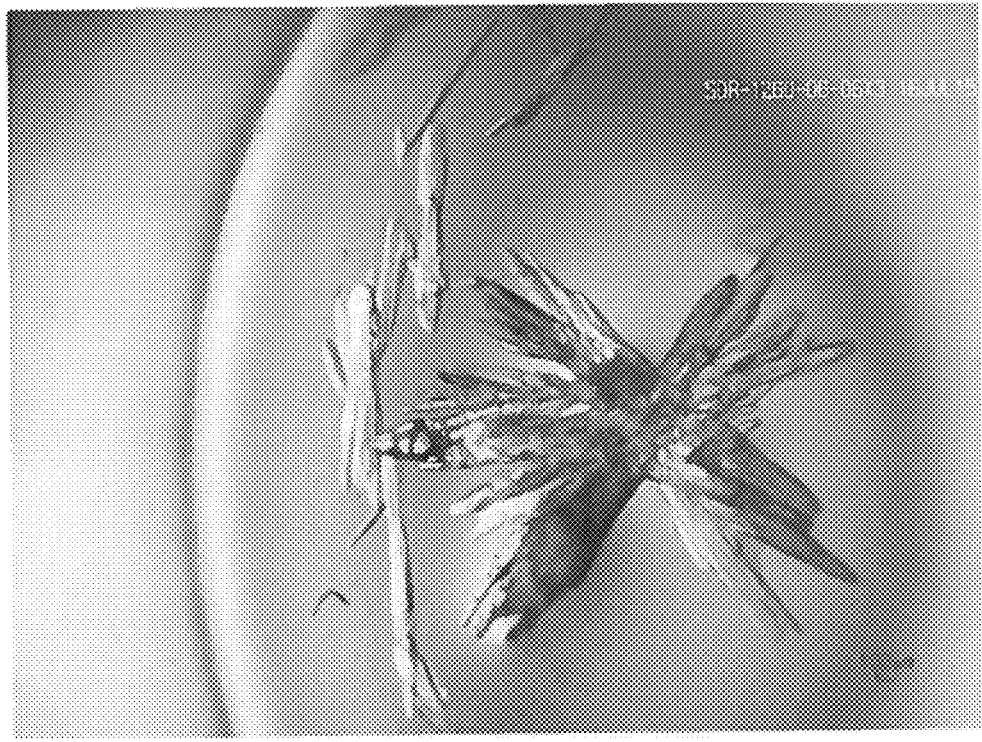
FIG. 2A-2B are an optical micrograph of the crystalline batch (FIG. 2A) and the crystal used for the data collection (FIG. 2B).
Figure 2B:
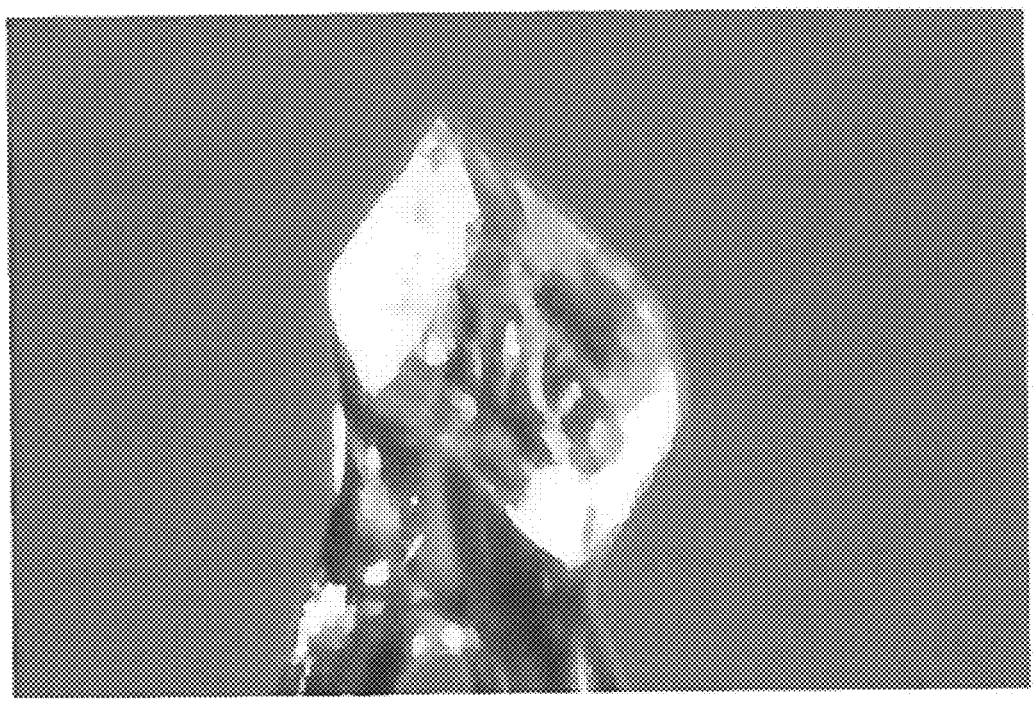

The following notation is applied: an embodiment of the invention is identified as Ei, where i is an integer indicating the number of the embodiment. An embodiment Ei' specifying a specific embodiment a previously listed embodiment Ei is identified as Ei'(Ei), e.g. E2(E1) means "in an embodiment E2 of embodiment E1".

Where an embodiment is a combination of two embodiments the notation is similarly Ei"(Ei and Ei'), e.g. E3(E2 and E1) means "in an embodiment E3 of any of embodiments E2 and E1"

Where an embodiment is a combination of more than two embodiments the notation is similarly Ei'"(Ei, Ei' and Ei"), e.g. E4(E1, E2 and E3) means "in an embodiment E4 of any of embodiments E1, E2 and E3"

In a first embodiment E1 the present invention relates to compounds having the following structure Compound (P1)

Compound (P2)

Compound (P3)

in racemic form and in enantiomerically enriched or pure form.

In an embodiment E2(E1) the enantiomerically pure variant of compound P3 is the first eluding compound when the racemic mixture of P3 is separated by Chiral HPLC (Column: Chiralpak IA, 250×4.6 mm×5 um; mobile phase Hex/EtOH/DEA=70:30:0.2) with a flow rate of 1.0 mL/min (P3 enantiomer 1).

E3(E1 and E2): A compound of any of E1 and E2 for the use as a medicament.

E4: A compound of any of E1 and E2 or the compound

Compound (P4)

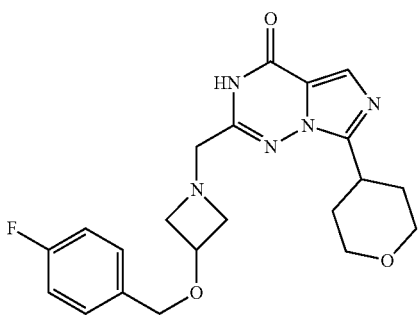

for use in the treatment of benign prostate hyperplasia or sickle cell disease.

E5: A pharmaceutical composition comprising a therapeutically effective amount of any of the compounds of E1 and E2 or the compound P4, and one or more pharmaceutically acceptable carriers, diluents or excipients.

E6(E5): The pharmaceutical is for the treatment of benign prostate hyperplasia or sickle cell disease.

E7: Use of the compound P4 or any of the compounds of E1 and E2 for the manufacture of a medicament for the treatment of benign prostate hyperplasia or sickle cell disease.

E8: A method of treating a subject suffering from benign prostate hyperplasia or sickle cell disease comprising administering a therapeutically effective amount of a compound P4 or any of the compounds of E1 and E2 to a subject in need thereof E9: A compound selected from the group consisting of 3-(4-fluorophenyl)-6-((3-(pyridin-4-yloxy)azetidin-1-yl)methyl)imidazo[1,5-a]pyrazin-8(7H)-one (P1), 6-[3-(pyridin-3-yloxy)-azetidin-1-ylmethyl]-3-(tetrahydro-pyran-4-yl)-7H-imidazo[1,5-a]pyrazin-8-one (P2), (3S,4S)-6-(4-methyl-1-pyrimidin-2-ylmethyl-pyrrolidin-3-yl)-3-(tetrahydro-pyran-4-yl)-7H-imidazo[1,5-a]pyrazin-8-one (P3, enantiomer 1), and (3R,4R)-6-(4-methyl-1-pyrimidin-2-ylmethyl-pyrrolidin-3-yl)-3-(tetrahydro-pyran-4-yl)-7H-imidazo[1,5-a]pyrazin-8-one (P3, enantiomer 2).

E10(E9) The compound (3S,4S)-6-(4-methyl-1-pyrimidin-2-ylmethyl-pyrrolidin-3-yl)-3-(tetrahydro-pyran-4-yl)-7H-imidazo[1,5-a]pyrazin-8-one (P3, enantiomer 1).

E11(E9) The compound (3R,4R)-6-(4-methyl-1-pyrimidin-2-ylmethyl-pyrrolidin-3-yl)-3-(tetrahydro-pyran-4-yl)-7H-imidazo[1,5-a]pyrazin-8-one (P3, enantiomer 2).

E12 (E9, E10 and E11) A compound of any of E9 to E11 for the use as a medicament.

E13: A compound selected from the group consisting of 3-(4-fluorophenyl)-6-((3-(pyridin-4-yloxy)azetidin-1-yl)methyl)imidazo[1,5-a]pyrazin-8(7H)-one (P1), 6-[3-(pyridin-3-yloxy)-azetidin-1-ylmethyl]-3-(tetrahydro-pyran-4-yl)-7H-imidazo[1,5-a]pyrazin-8-one (P2), (3S,4S)-6-(4-methyl-1-pyrimidin-2-ylmethyl-pyrrolidin-3-yl)-3-(tetrahydro-pyran-4-yl)-7H-imidazo[1,5-a]pyrazin-8-one (P3, enantiomer 1), (3R,4R)-6-(4-methyl-1-pyrimidin-2-ylmethyl-pyrrolidin-3-yl)-3-(tetrahydro-pyran-4-yl)-7H-imidazo[1,5-a]pyrazin-8-one (P3, enantiomer 2) and 2-[3-(4-fluoro-phenoxy)-azetidin-1-ylmethyl]-7-(tetrahydro-pyran-4-yl)-3H-imidazo[5,1-f][1,2,4]triazin-4-one (P4) for use in the treatment of benign prostate hyperplasia or sickle cell disease.

E14: A pharmaceutical composition comprising a therapeutically effective amount of any of the compounds 3-(4-fluorophenyl)-6-((3-(pyridin-4-yloxy)azetidin-1-yl)methyl)imidazo[1,5-a]pyrazin-8(7H)-one (P1), 6-[3-(pyridin-3-yloxy)-azetidin-1-ylmethyl]-3-(tetrahydro-pyran-4-yl)-7H-imidazo[1,5-a]pyrazin-8-one (P2), (3S,4S)-6-(4-methyl-1-pyrimidin-2-ylmethyl-pyrrolidin-3-yl)-3-(tetrahydro-pyran-4-yl)-7H-imidazo[1,5-a]pyrazin-8-one (P3, enantiomer 1), (3R,4R)-6-(4-methyl-1-pyrimidin-2-ylmethyl-pyrrolidin-3-yl)-3-(tetrahydro-pyran-4-yl)-7H-imidazo[1,5-a]pyrazin-8-one (P3, enantiomer 2) and 2-[3-(4-fluoro-phenoxy)-azetidin-1-ylmethyl]-7-(tetrahydro-pyran-4-yl)-3H-imidazo[5,1-f][1,2,4]triazin-4-one (P4), and one or more pharmaceutically acceptable carriers, diluents or excipients E15(E14): The pharmaceutical is for the treatment of benign prostate hyperplasia or sickle cell disease.

E16: Use of any of the compounds 3-(4-fluorophenyl)-6-((3-(pyridin-4-yloxy)azetidin-1-yl)methyl)imidazo[1,5-a]pyrazin-8(7H)-one (P1), 6-[3-(pyridin-3-yloxy)-azetidin-1-ylmethyl]-3-(tetrahydro-pyran-4-yl)-7H-imidazo[1,5-a]pyrazin-8-one (P2), (3S,4S)-6-(4-methyl-1-pyrimidin-2-ylmethyl-pyrrolidin-3-yl)-3-(tetrahydro-pyran-4-yl)-7H-imidazo[1,5-a]pyrazin-8-one (P3, enantiomer 1), (3R,4R)-6-(4-methyl-1-pyrimidin-2-ylmethyl-pyrrolidin-3-yl)-3-(tetrahydro-pyran-4-yl)-7H-imidazo[1,5-a]pyrazin-8-one (P3, enantiomer 2) and 2-[3-(4-fluoro-phenoxy)-azetidin-1-ylmethyl]-7-(tetrahydro-pyran-4-yl)-3H-imidazo[5,1-f][1,2,4]triazin-4-one (P4) for the manufacture of a medicament for the treatment of benign prostate hyperplasia or sickle cell disease.

E17: A method of treating a subject suffering from benign prostate hyperplasia or sickle cell disease comprising administering a therapeutically effective amount of any of the compounds 3-(4-fluorophenyl)-6-((3-(pyridin-4-yloxy)azetidin-1-yl)methyl)imidazo[1,5-a]pyrazin-8(7H)-one (P1), 6-[3-(Pyridin-3-yloxy)-azetidin-1-ylmethyl]-3-(tetrahydro-pyran-4-yl)-7H-imidazo[1,5-a]pyrazin-8-one (P2), (3S,4S)-6-(4-methyl-1-pyrimidin-2-ylmethyl-pyrrolidin-3-yl)-3-(tetrahydro-pyran-4-yl)-7H-imidazo[1,5-a]pyrazin-8-one (P3, enantiomer 1), (3R,4R)-6-(4-methyl-1-pyrimidin-2-ylmethyl-pyrrolidin-3-yl)-3-(tetrahydro-pyran-4-yl)-7H-imidazo[1,5-a]pyrazin-8-one (P3, enantiomer 2) and 2-[3-(4-fluoro-phenoxy)-azetidin-1-ylmethyl]-7-(tetrahydro-pyran-4-yl)-3H-imidazo[5,1-f][1,2,4]triazin-4-one (P4) to a subject in need thereof.

PDE9 Inhibitors

In the context of the present invention a compound is considered to be a PDE9 inhibitor if the amount required to reach the $IC_{50}$ level of any of the three PDE9 isoforms is 10 micro molar or less, preferably less than 9 micro molar, such as 8 micro molar or less, such as 7 micro molar or less, such as 6 micro molar or less, such as 5 micro molar or less, such as 4 micro molar or less, such as 3 micro molar or less, more preferably 2 micro molar or less, such as 1 micro molar or less, in particular 500 nM or less. In preferred embodiments the required amount of PDE9 inhibitor required to reach the $IC_{50}$ level of PDE9 is 400 nM or less, such as 300 nM or less, 200 nM or less, 100 nM or less, or even 80 nM or less, such as 50 nM or less, for example 25 nM or less.

Throughout this application the notations $IC_{50}$ and IC50 are used interchangeably.

Isomeric Forms

Where compounds of the present invention contain one or more chiral centers reference to any of the compounds will, unless otherwise specified, cover the enantiomerically or diastereomerically pure compound as well as mixtures of the enantiomers or diastereomers in any ratio.

Pharmaceutically Acceptable Salts

The present invention also comprises salts of the compounds, typically, pharmaceutically acceptable salts. Such salts include pharmaceutically acceptable acid addition salts. Acid addition salts include salts of inorganic acids as well as organic acids.

Representative examples of suitable inorganic acids include hydrochloric, hydrobromic, hydroiodic, phosphoric, sulfuric, sulfamic, nitric acids and the like. Representative examples of suitable organic acids include formic, acetic, trichloroacetic, trifluoroacetic, propionic, benzoic, cinnamic, citric, fumaric, glycolic, itaconic, lactic, methanesulfonic, maleic, malic, malonic, mandelic, oxalic, picric, pyruvic, salicylic, succinic, methane sulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, theophylline acetic acids, as well as the 8-halotheophyllines, for example 8-bromotheophylline and the like. Further examples of pharmaceutically acceptable inorganic or organic acid addition salts include the pharmaceutically acceptable salts listed in Berge, S. M. et al., J. Pharm. Sci. 1977, 66, 2, the contents of which are hereby incorporated by reference.

Furthermore, the compounds of this invention may exist in unsolvated as well as in solvated forms with pharmaceutically acceptable solvents such as water, ethanol and the like. In general, the solvated forms are considered equivalent to the unsolvated forms for the purposes of this invention.

Pharmaceutical Composition

The present invention further provides a pharmaceutical composition comprising a therapeutically effective amount of any of the compounds of the present invention and a pharmaceutically acceptable carrier or diluent. The present invention also provides a pharmaceutical composition comprising a therapeutically effective amount of one of the specific compounds disclosed in the Experimental Section herein and a pharmaceutically acceptable carrier or diluent.

The compounds of the invention may be administered alone or in combination with pharmaceutically acceptable carriers, diluents or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 22nd Edition, Gennaro, Ed., Mack Publishing Co., Easton, Pa., 2013.

The pharmaceutical compositions may be specifically formulated for administration by any suitable route such as oral, rectal, nasal, pulmonary, topical (including buccal and sublingual), transdermal, intracisternal, intraperitoneal, vaginal and parenteral (including subcutaneous, intramuscular, intrathecal, intravenous and intradermal) routes. It will be appreciated that the route will depend on the general condition and age of the subject to be treated, the nature of the condition to be treated and the active ingredient.

Pharmaceutical compositions for oral administration include solid dosage forms such as capsules, tablets, dragees, pills, lozenges, powders and granules. Where appropriate, the compositions may be prepared with coatings such as enteric coatings or they may be formulated so as to provide controlled release of the active ingredient such as sustained or prolonged release according to methods well known in the art. Liquid dosage forms for oral administration include solutions, emulsions, suspensions, syrups and elixirs.

Pharmaceutical compositions for parenteral administration include sterile aqueous and nonaqueous injectable solutions, dispersions, suspensions or emulsions as well as sterile powders to be reconstituted in sterile injectable solutions or dispersions prior to use. Other suitable administration forms include, but are not limited to, suppositories, sprays, ointments, creams, gels, inhalants, dermal patches and implants.

Typical oral dosages range from about 0.001 to about 100 mg/kg body weight per day. Typical oral dosages also range from about 0.01 to about 50 mg/kg body weight per day. Typical oral dosages further range from about 0.05 to about 10 mg/kg body weight per day. Oral dosages are usually administered in one or more dosages, typically, one to three dosages per day. The exact dosage will depend upon the frequency and mode of administration, the gender, age, weight and general condition of the subject treated, the nature and severity of the condition treated and any concomitant diseases to be treated and other factors evident to those skilled in the art.

The formulations may also be presented in a unit dosage form by methods known to those skilled in the art. For illustrative purposes, a typical unit dosage form for oral administration may contain from about 0.01 to about 1000 mg, from about 0.05 to about 500 mg, or from about 0.5 mg to about 200 mg.

For parenteral routes such as intravenous, intrathecal, intramuscular and similar administration, typical doses are in the order of half the dose employed for oral administration.

The present invention also provides a process for making a pharmaceutical composition comprising admixing a therapeutically effective amount of a compound of the present invention and at least one pharmaceutically acceptable carrier or diluent. In an embodiment, of the present invention, the compound utilized in the aforementioned process is one of the specific compounds disclosed in the Experimental Section herein.

The compounds of this invention are generally utilized as the free substance or as a pharmaceutically acceptable salt thereof. Such salts are prepared in a conventional manner by treating a solution or suspension of a compound of the present invention with a molar equivalent of a pharmaceutically acceptable acid. Representative examples of suitable organic and inorganic acids are described above.

For parenteral administration, solutions of the compounds of the present invention in sterile aqueous solution, aqueous propylene glycol, aqueous vitamin E or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The compounds of the present invention may be readily incorporated into known sterile aqueous media using standard techniques known to those skilled in the art.

Suitable pharmaceutical carriers include inert solid diluents or fillers, sterile aqueous solutions and various organic solvents. Examples of solid carriers include lactose, terra alba, sucrose, cyclodextrin, talc, gelatin, agar, pectin, acacia, magnesium stearate, stearic acid and lower alkyl ethers of cellulose. Examples of liquid carriers include, but are not limited to, syrup, peanut oil, olive oil, phospholipids, fatty acids, fatty acid amines, polyoxyethylene and water. Similarly, the carrier or diluent may include any sustained release material known in the art, such as glyceryl monostearate or glyceryl distearate, alone or mixed with a wax.

The pharmaceutical compositions formed by combining the compounds of the present invention and a pharmaceutically acceptable carrier are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and optionally a suitable excipient.

Furthermore, the orally available formulations may be in the form of a powder or granules, a solution or suspension in an aqueous or non-aqueous liquid, or an oil-in-water or water-in-oil liquid emulsion.

If a solid carrier is used for oral administration, the preparation may be tabletted, placed in a hard gelatine capsule in powder or pellet form or it may be in the form of a troche or lozenge. The amount of solid carrier will vary widely but will range from about 25 mg to about 1 g per dosage unit. If a liquid carrier is used, the preparation may be in the form of a syrup, emulsion, soft gelatine capsule or sterile injectable liquid such as an aqueous or non-aqueous liquid suspension or solution.

The pharmaceutical compositions of the invention may be prepared by conventional methods in the art. For example, tablets may be prepared by mixing the active ingredient with ordinary adjuvants and/or diluents and subsequently compressing the mixture in a conventional tabletting machine prepare tablets. Examples of adjuvants or diluents comprise: corn starch, potato starch, talcum, magnesium stearate, gelatin, lactose, gums, and the like. Any other adjuvants or additives usually used for such purposes such as colorings, flavorings, preservatives etc. may be used provided that they are compatible with the active ingredients.

Compounds of the Invention

Table 1 lists compounds of the invention and the corresponding IC50 values (nM) determined as described in the section "PDE9 inhibition assay". Further, the concentration of compounds in plasma and brain, determined as described in the section "Blood Brain Barrier penetration", are listed. Each of the compounds constitutes an individual embodiment of the present invention:

TABLE 1

Compounds of the invention, IC50 values and plasma/brain concentration

| Compound | PDE9 IC50 (nM) | PDE1 IC50 (nM) | Plasma concentration after 30 minutes and 120 minutes (ng/mL) | Brain concentration after 30 minutes and 120 minutes (ng/mL) | Brain/Plasma ratio after 30 minutes and 120 minutes |
|---|---|---|---|---|---|
| Compound (P1) | 42 | 45090 | 30 min.: 719<br>120 min.: 86 | 30 min.: 42<br>120 min.: 7 | 0.06<br>0.08 |
| Compound (P2) | 36 | 5283 | 30 min.: 715<br>120 min.: 11 | Below detection limit | Not calculated (brain concentration below limit of detection) |
| Compound (P3, enantiomer 1) | 49 | 3000 | 30 min.: 1620<br>120 min.: 226 | 30 min.: 67<br>120 min.: 7 | 0.04<br>0.03 |
| Compound (P4) | 10 | 1009 | 30 min.: 3380<br>120 min. 352 | 30 min.: 125<br>120 min.: 15 | 0.04<br>0.04 |
| 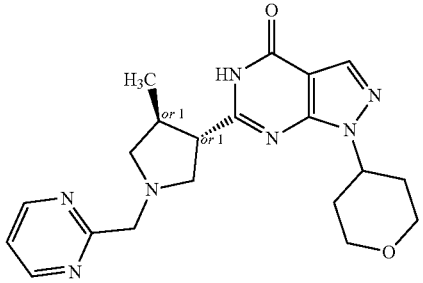 [SMILES: C[C@@H]1CN(Cc2ncccn2)C[C@H]1c1nc2c(cnn2C2CCOCC2)c(=O)[nH]1] | 70 | 2500 | 30 min.: 1230<br>120 min.: 529 | 30 min.: 500<br>120 min.: 215 | 0.41<br>0.41 |

Reference compound disclosed in WO2008/139293

EXAMPLES

Example 1

Synthesis of the Compounds

The compounds of the present invention may be synthesized as described below.

Overview Schemes:

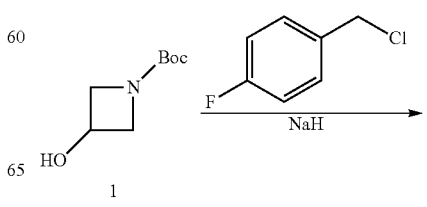

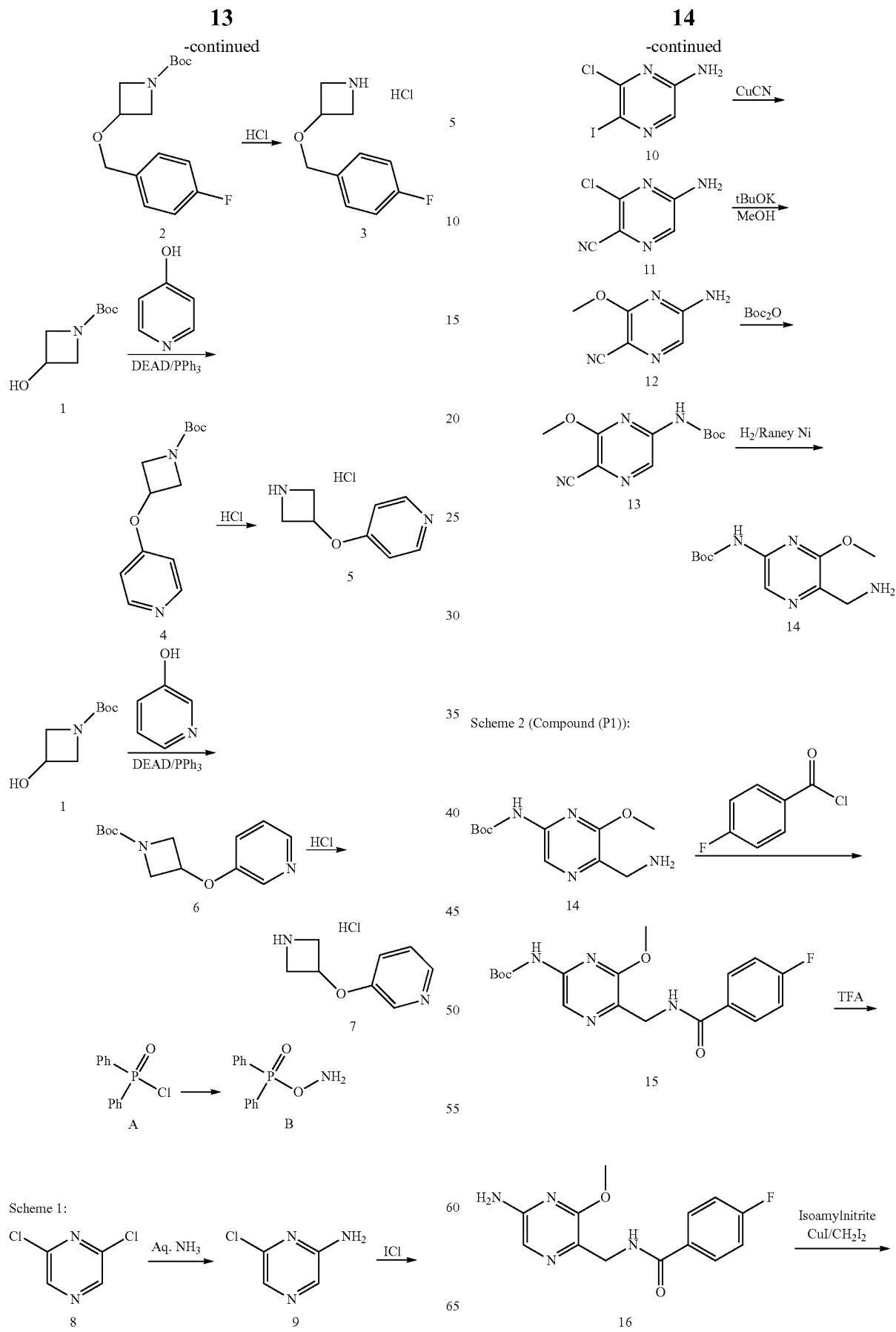

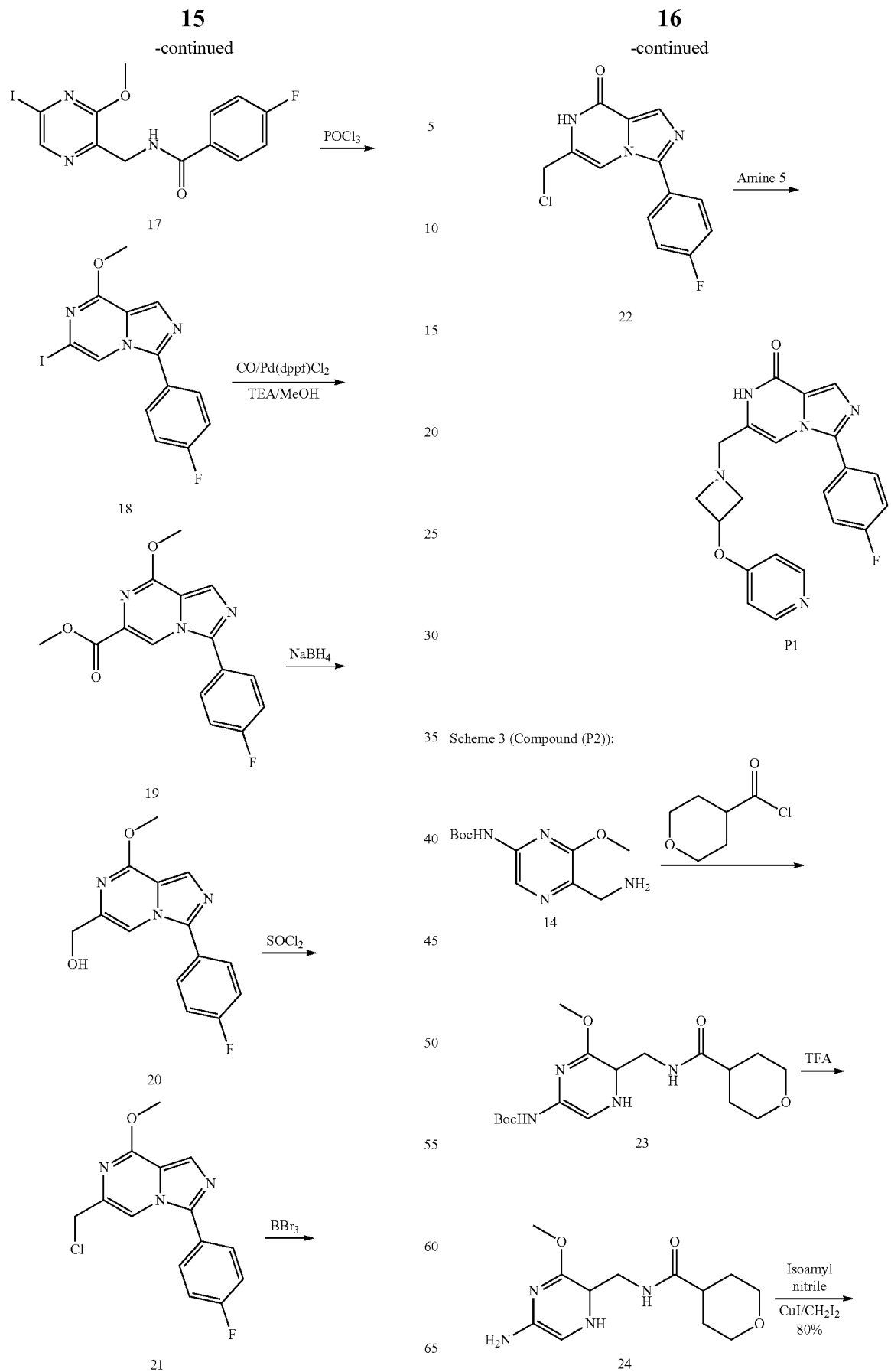
Scheme 3 (Compound (P2)):

17
-continued
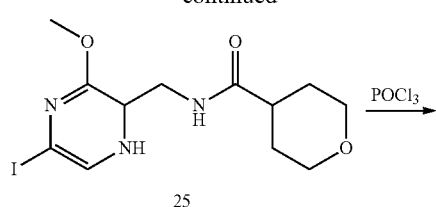
25
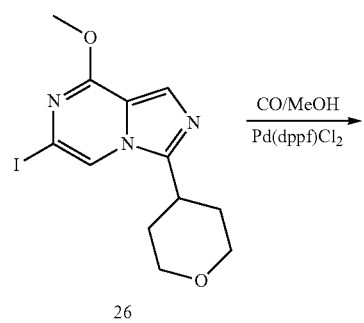
26
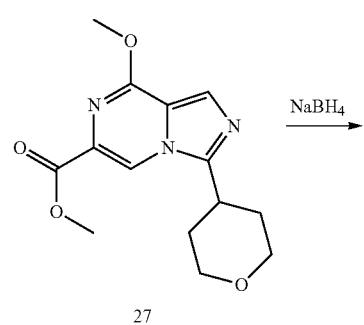
27
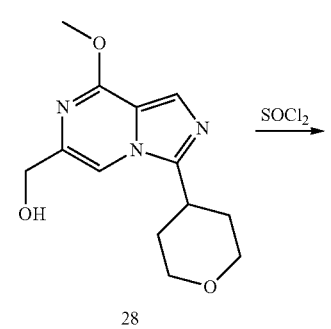
28
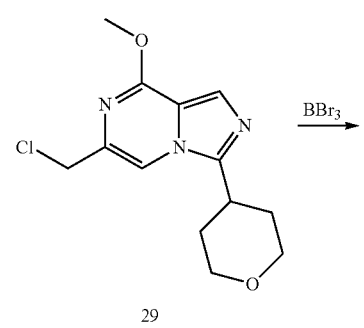
29
18
-continued
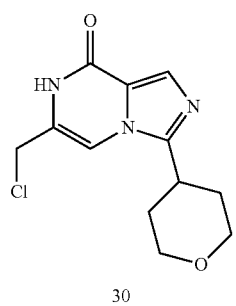
30
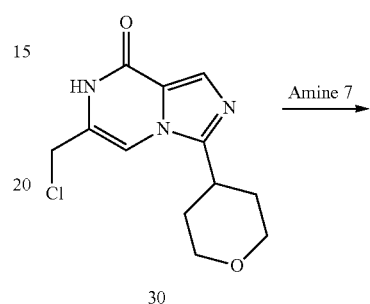
30
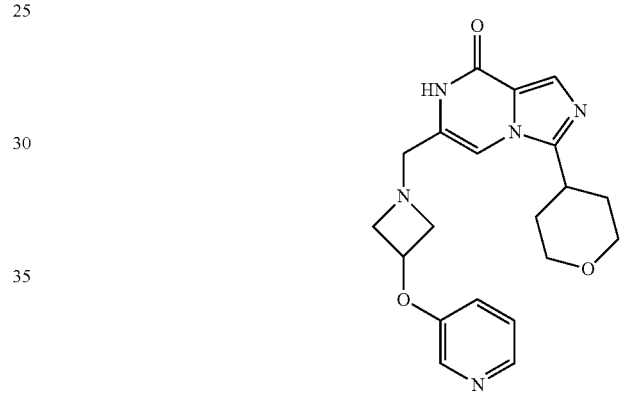
P2
Scheme 4 (Compound (P3)):
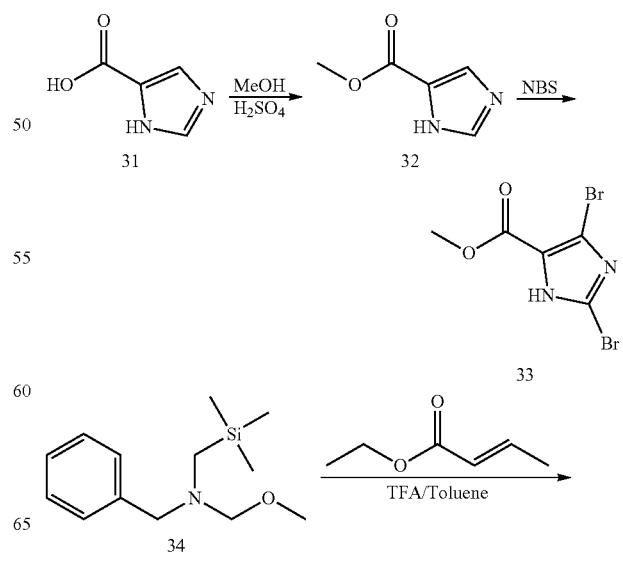

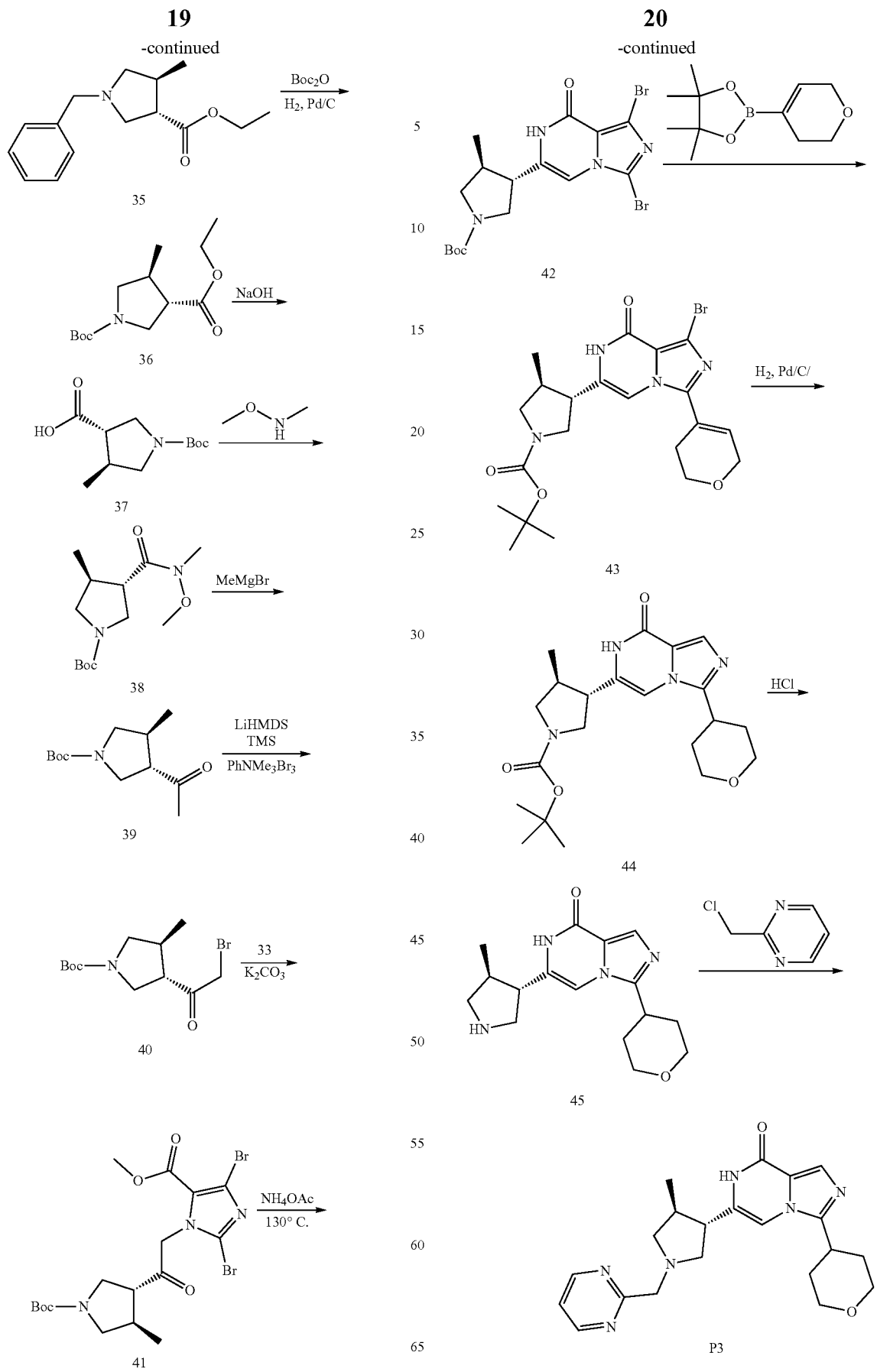

Scheme 5 ((Compound (P4)):

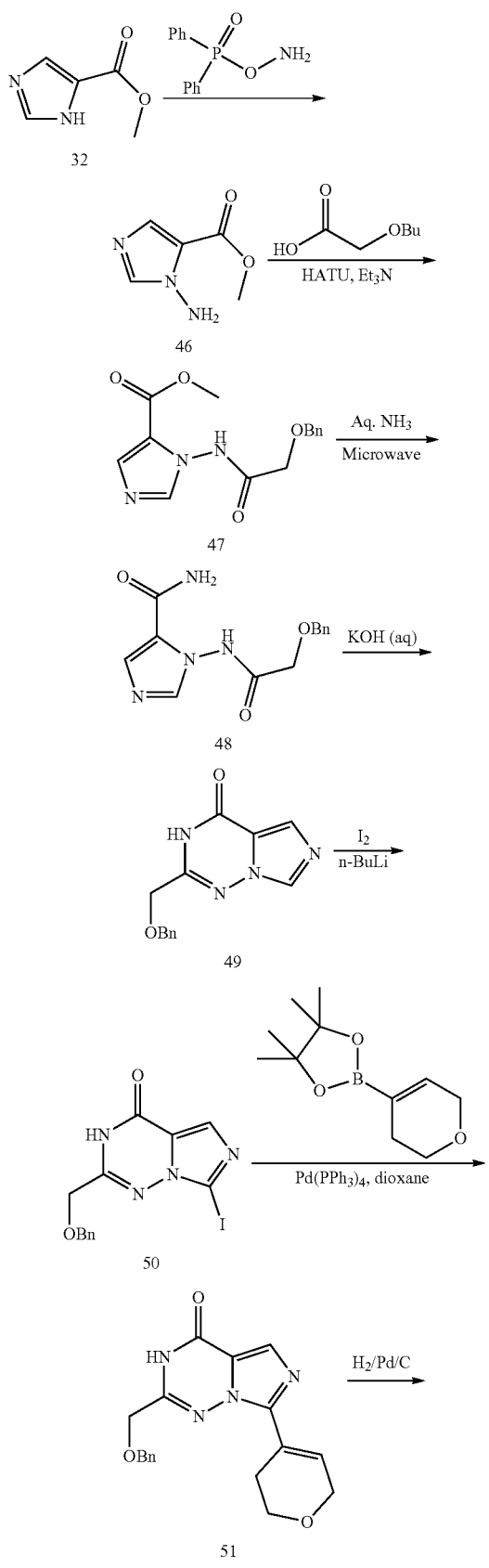
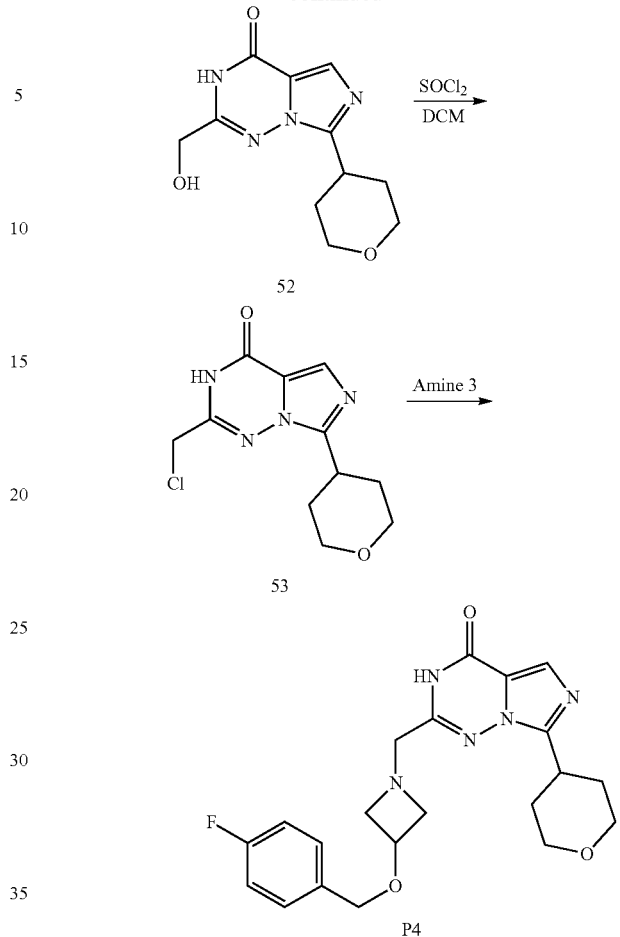

P4

Synthetic Procedures

List of Abbreviations aq aqueous
NBS N-bromosuccinimide
Boc tert-Butoxycarbonyl
° C. degrees Celsius
CDI N,N-carbonyl dimidazole
$\delta_H$ chemical shift in parts per million downfield from tetramethylsilane
DCM dichloromethane
DEAD diethyl azodicarboxylate
Dppf bis(diphenylphosphino)ferrocene
DIPEA N,N-diisopropylethylamine
DMF N,N-dimethylformamide
eq equivalent
ESI electrospray ionization
Et ethyl
EtOAc ethyl acetate
g gram(s)
HPLC high-performance liquid chromatography
h hours
Hz hertz
J coupling constant (in NMR spectrometry)
LCMS liquid chromatography mass spectrometry
LiHMDS Lithium bis(trimethylsilyl)amide
μ micro m multiplet (spectral); meter(s); milli
M+ parent molecular ion
Me methyl
MeCN acetonitrile
MeOH methanol
MHz megahertz
min minute(s)
mL milliliter
MS mass spectrometry
MTBE Methyl-tert-butyl ether
N normal (equivalents per liter)
NaOH sodium hydroxide
NBS N-Bromosuccinimide
nm nanometer(s)
NMR nuclear magnetic resonance
PE petroleum ether bp: 60~90° C.
rt room temperature
s singlet (spectral)
t triplet (spectral)
T temperature
TEA triethylamine
TFA trifluoroacetic acid
THF tetrahydrofuran
TLC thin layer chromatography
TMS tetramethylsilane
TMS-Cl trimethylsilyl chloride
Tol toluene General Experimental Methods $^1$H NMR spectra were recorded on Bruker Avance III 400 MHz and Bruker Fourier 300 MHz and TMS was used as an internal standard.

LCMS was taken on a quadrupole Mass Spectrometer on Agilent LC/MSD 1200 Series (Column: ODS 2000 (50×4.6 mm, 5 μm) operating in ES (+) or (−) ionization mode; T=30° C.; flow rate=1.5 mL/min; detected wavelength: 214 nm.

Synthesis of 6-Chloro-pyrazin-2-ylamine (9)

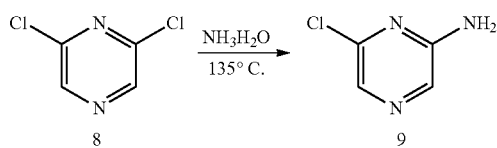

A solution of compound 8 (450.0 g, 3.02 mol) in conc. aq. NH$_3$ (3.0 L) was stirred at 135° C. overnight in a 10 L sealed pressure vessel. TLC and LC/MS showed complete conversion of the starting material. The reaction mixture was cooled to room temperature and filtered to afford a white solid. The solid was washed with water (200 mL×3), and then dried to afford compound 9 (312 g, 80% yield) as a solid.

$^1$HNMR (400 MHz, DMSO-d6): δ 7.82 (s, 1 H), 7.12 (s, 1 H), 6.93 (s, 2H). MS Calcd.: 129 MS Found: 130 ([M+H]$^+$).

Synthesis of 6-Chloro-5-iodo-pyrazin-2-ylamine (10)

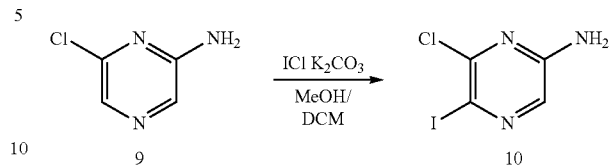

To a mixture of compound 9 (312.0 g, 2.4 mol) and K$_2$CO$_3$ (664.0 g, 4.8 mol) in MeOH (1.0 L) was dropwise added ICl (704.0 g, 4.3 mol in 1.0 L of DCM) over 2 hours at 0° C. Then the reaction mixture was stirred at room temperature overnight. The reaction was quenched with Na$_2$SO$_3$ aqueous solution (2M, 1.5 L). The mixture was extracted with DCM (1.0 L×3). The combined organic phases were dried over anhydrous Na$_2$SO$_4$, filtered and concentrated. The crude product was purified by column chromatography on silica gel (PE/EA=10/1 to 4/1) to afford compound 10 (460 g, 75% yield) as a solid.

$^1$HNMR (400 MHz, DMSO-d6): δ 7.68 (s, 1H), 7.07 (s, 2H). MS Calcd.: 255 MS Found: 256 ([M+H]$^+$).

Synthesis of 5-Amino-3-chloro-pyrazine-2-carbonitrile (11)

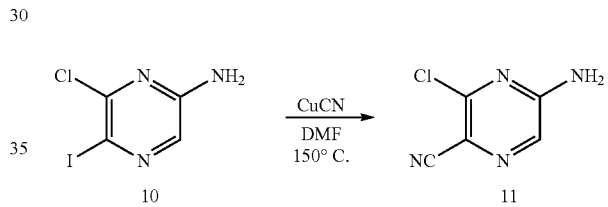

A mixture of compound 10 (460.0 g, 1.8 mol) and CuCN (177.0 g, 1.98 mol) in DMF (2.0 L) was stirred on an oil bath at 150° C. for 2 hours. LC/MS showed full conversion of the starting martial. The reaction mixture was cooled to room temperature and poured into EtOAc (1.5 L). To the resulting mixture was slowly added conc. aq. NH$_3$ (1.0 L), and it was then extracted with EtOAc (1.0 L×2). The combined organic phases were washed with H$_2$O (1.5 L×5) and brine (1.5 L) and dried over anhydrous Na$_2$SO$_4$. The organic phase was filtered and concentrated to afford compound 11 (232 g, 84% yield) as solid.

$^1$HNMR (400 MHz, DMSO-d6): δ 8.12 (s, 2H), 7.88 (s, 1H). MS Calcd.: 154; MS Found: 155 ([M+H]$^+$).

Synthesis of 5-Amino-3-methoxy-pyrazine-2-carbonitrile (12)

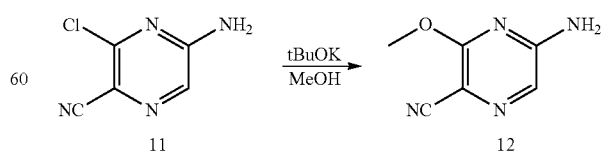

Potassium tert-butoxide (168.0 g, 1.5 mol) was added in portions into methanol (1.5 L) in a round-bottom flask. The suspension was refluxed for one hour. Then compound 11

(232.0 g, 1.5 mol) was added under an $N_2$ atmosphere. The resulting suspension was refluxed for 1.5 hours. After cooling to room temperature the reaction mixture was concentrated in vacuum and diluted with water (2.0 L), then extracted with EtOAc (2.0 L×5). The combined organic phases were dried with $Na_2SO_4$, filtered and concentrated to afford 12 (170 g, 75% yield) as a solid.

$^1$HNMR (300 MHz, DMSO-d6): δ 7.69 (s, 2H), 7.51 (s, 1H), 3.89 (s, 3H). MS Calcd.: 150; MS Found: 151 ([M+H]$^+$).

Synthesis of (5-Cyano-6-methoxy-pyrazin-2-yl)-carbamic acid tert-butyl ester (13)

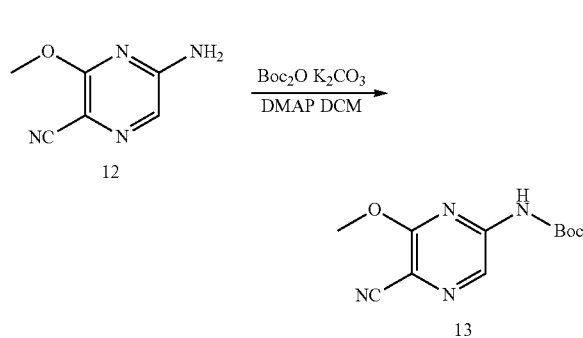

4-Dimethylaminopyridine (1.0 g, 0.01 mol) was added into a mixture of compound 12 (120.0 g, 0.8 mol) in DCM (1.5 L) at room temperature. Then di-tert-butyl dicarbonate (327 g, 1.5 mol) in DCM (1.0 L) was added dropwise at 10-20° C. for 2 hours. Then the reaction was stirred at room temperature overnight. The suspension dissolved and the reaction solution was diluted with 2 L of water. The DCM phase was separated and dried with sodium sulfate, filtered and concentrated in vacuum. The residue was purified by column chromatography on silica gel (PE/EtOAc=10:1) to afford 13 (150 g, 75% yield).

$^1$HNMR (300 MHz, DMSO-d6): δ 10.78 (s, 1H), 8.70 (s, 1H), 3.97 (s, 3H), 1.49 (s, 9H). MS Calcd.: 250; MS Found: 251 ([M+H]$^+$).

Synthesis of (5-Aminomethyl-6-methoxy-pyrazin-2-yl)-carbamic acid tert-butyl ester (14)

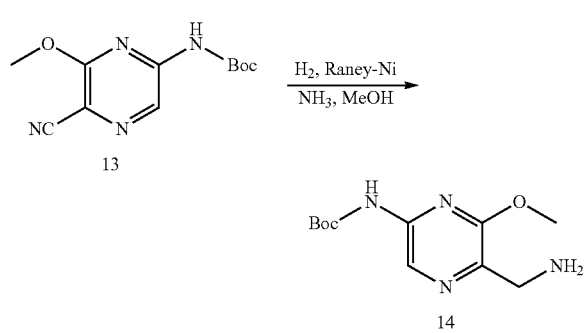

Raney Ni (10.0 g) was added into a mixture of compound 13 (30.0 g, 120 mmol) in concentrated $NH_3$ in MeOH (500 mL) at room temperature. The suspension was stirred at room temperature under 1 atm $H_2$ overnight. The reaction mixture was diluted with a mixture of DCM/MeOH (1:1). The reaction mixture was filtered and the filtrate was concentrated in vacuum. The residue was triturated with PE/EtOAc=2/1 to afford 14 (23 g, 75% yield) as a solid.

$^1$HNMR (300 MHz, DMSO-d6): δ 8.46 (s, 1H), 3.87 (s, 3H), 3.70 (s, 2H), 3.17 (s, 3H), 1.47 (s, 9H). MS Calcd.: 254; MS Found: 255 ([M+H]$^+$).

Synthesis of 5-[(4-Fluoro-benzoylamino)-methyl]-6-methoxy-pyrazin-2-yl-carbamic acid tert-butyl ester (15)

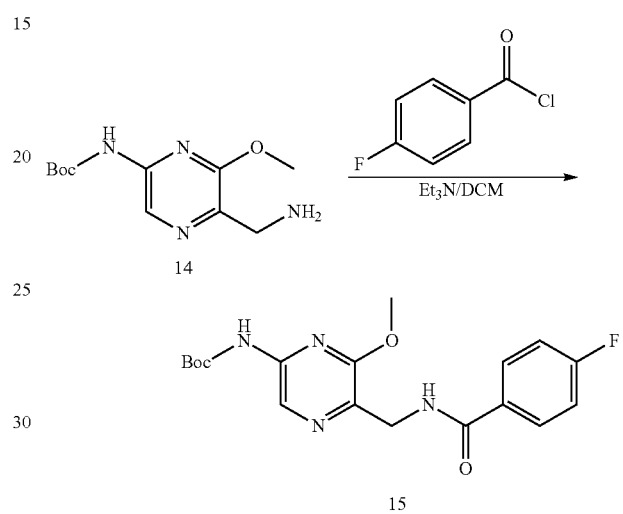

To a solution of compound 14 (4.52 g, 17.86 mmol) in DCM (200 mL) was added TEA (5.41 g, 58.53 mmol), then 4-fluorobenzoyl chloride (3.4 g, 21.42 mmol) was added dropwise. The resulting reaction mixture was stirred at room temperature for 2 hours. TLC detected the reaction was complete. The reaction was quenched with water (100 mL). The organic phase was separated and the aqueous phase was extracted with DCM (200 mL×2). The combined organic phases were dried over anhydrous $MgSO_4$, filtered and concentrated in vacuum. The residue was purified by column chromatography on silica gel to afford 15 (5.77 g, 85.9% yield) as a solid.

$^1$HNMR (400 MHz, DMSO-d6): δ 9.89 (s, 1 H), 8.81 (t, J=5.6 Hz, 1 H), 8.46 (s, 1 H), 7.94 (m, 2 H), 7.29 (m, 2 H), 4.49 (d, J=5.6 Hz, 2 H), 3.90 (s, 3 H), 1.47 (s, 9 H). MS Calcd.: 376; MS Found: 377 ([M+H]$^+$).

Synthesis of N-(5-Amino-3-methoxy-pyrazin-2-ylmethyl)-4-fluoro-benzamide (16)

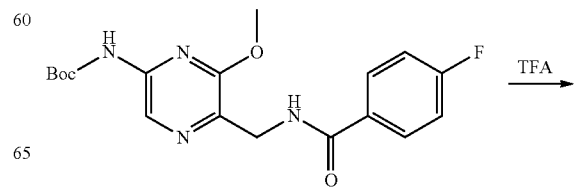

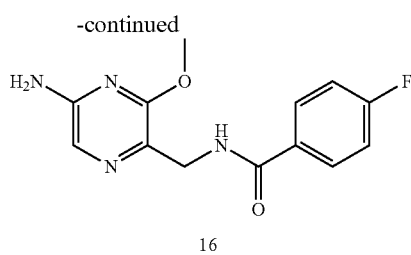

16

Compound 15 (5.77 g, 15.33 mmol) was dissolved in DCM (25 mL). TFA (25 mL) was added. The reaction was stirred at room temperature overnight. TLC detected the reaction was complete. The solvent was removed. The residue was diluted with DCM (100 mL) and saturated NaHCO₃ aqueous solution (100 mL). The organic phase was separated and the aqueous phase was extracted with DCM (100 mL×2). The combined organic phases were dried over anhydrous MgSO₄, filtered and concentrated in vacuum. The residue was purified by column chromatography on silica gel (eluted with PE/EtOAc=6:1 to 1:1) to afford 16 (3.9 g, 92.2% yield) as a solid.

¹HNMR (300 MHz, CDCl₃): δ 7.90-7.85 (m, 2 H), 7.46 (s, 1 H), 7.40 (t, J=6.0 Hz, 1 H), 7.11 (m, 2 H), 4.60 (d, J=6.0 Hz, 2 H), 4.37 (s, 2 H), 3.93 (s, 3 H). MS Calcd.: 276; MS Found: 277 ([M+H]⁺).

Synthesis of 4-Fluoro-N-(5-iodo-3-methoxy-pyrazin-2-ylmethyl)-benzamide (17)

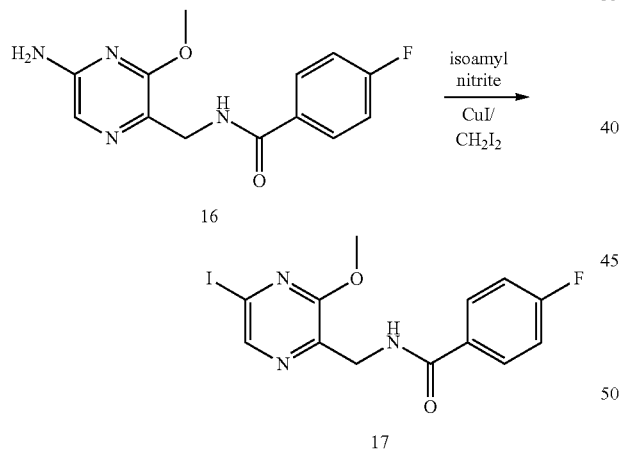

Compound 16 (3.9 g, 14.1 mmol) was dissolved in anhydrous THF (100 mL). CuI (2.7 g, 14.1 mmol), then isoamyl nitrite (4.9 g, 42.3 mmol) and CH₂I₂ (3.8 g, 14.1 mmol) were added under N₂ gas atmosphere. The reaction mixture was heated at 75° C. for 3 hours. Then the reaction was cooled to room temperature and filtered. The filtrate was concentrated in vacuum. The residue was purified by column chromatography on silica gel (eluted with PE/EtOAc 5:1) to afford 17 (2.0 g, 37% yield) as a solid.

¹HNMR (400 MHz, CDCl₃): δ 8.34 (s, 1 H), 7.88 (m, 2 H), 7.36 (t, J=4.4 Hz, 1 H), 7.14 (m, 2 H), 4.66 (d, J=4.4 Hz, 2 H), 4.04 (s, 3 H). MS Calcd.: 387; MS Found: 388 ([M+H]⁺).

Synthesis of 3-(4-Fluoro-phenyl)-6-iodo-8-methoxy-imidazo[1,5-a]pyrazine (18)

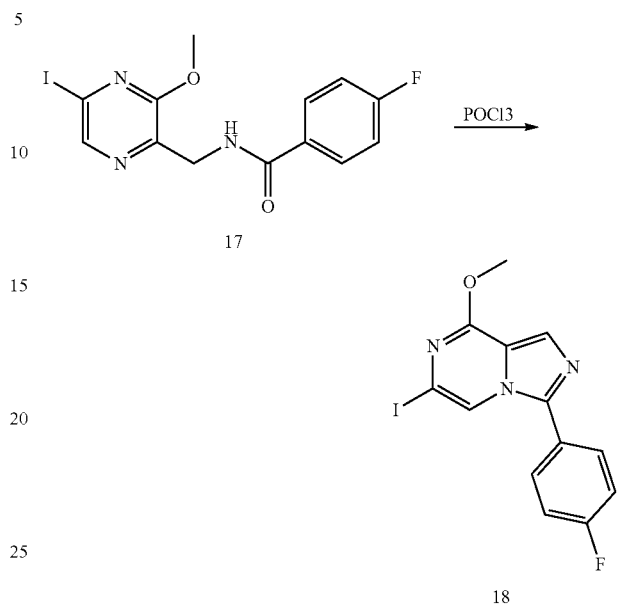

Compound 17 (1.6 g, 4.13 mmol) was suspended in MeCNCH₃CN (50 mL). POCl₃ (6.3 g, 41.3 mmol) and TEA (1.25 g, 12.39 mmol) was added under N₂ gas atmosphere and the reaction mixture was heated at 85° C. for 6 hours. The solvent was removed under reduced pressure. The residue was diluted with DCM (100 mL) and ice-water (30 mL). Then saturated Na₂CO₃ aqueous solution (100 mL) was added. The organic phase was separated and the aqueous phase was extracted with DCM (100 mL×2). The combined organic phases were dried, filtered and concentrated in vacuum. The residue was purified by column chromatography on silica gel (eluted with PE/EtOAc=20:1 to 3:1) to afford 18 (1.5 g, 97.8% yield) as a solid.

¹HNMR (300 MHz, CDCl₃): δ 8.01 (s, 1 H), 7.82 (s, 1 H), 7.77-7.72 (m, 2 H), 7.28-7.23 (m, 2 H), 4.11 (s, 3 H). MS Calcd.: 369; MS Found: 370 ([M+H]⁺).

Synthesis of 3-(4-Fluoro-phenyl)-8-methoxy-imidazo[1,5-a]pyrazine-6-carboxylic acid methyl ester (19)

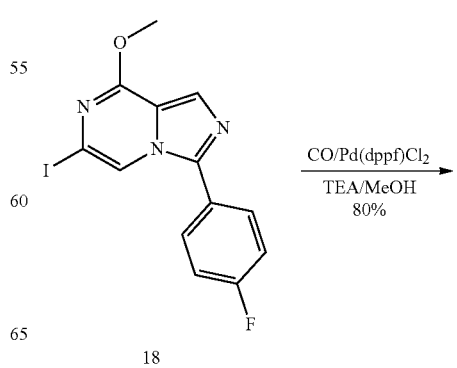

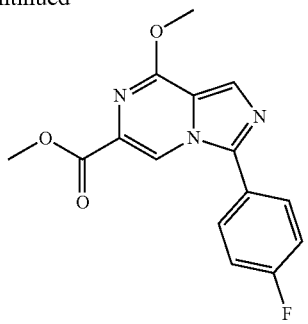

19

To a mixture solution of 18 (4.11 g, 11.13 mmol), CuI (640 mg, 3.34 mmol) and Pd(dppf)$_2$Cl$_2$ (930 mg, 1.11 mmol) in MeOH (100 mL) was added TEA (14 mL). The reaction mixture was heated to 85° C. under a CO atmosphere (3.0 MPa) for 16 hours. The reaction mixture was allowed to cool to room temperature and concentrated in vacuo to get the crude product. The residue was purified by column chromatography on silica gel (eluted with PE/EtOAc=1:1) to afford 19 (2.3 g, 75% yield) as a solid.

$^1$H NMR (400 MHz, CDCl$_3$): δ 8.59 (s, 1 H), 7.87 (s, 1 H), 7.78 (m, 2 H), 7.28 (m, 2 H), 4.21 (s, 3 H), 3.96 (s, 3 H). MS Calcd.: 301; MS Found: 302 ([M+H]$^+$).

Synthesis of [3-(4-Fluoro-phenyl)-8-methoxy-imidazo[1,5-a]pyrazin-6-yl]-methanol (20)

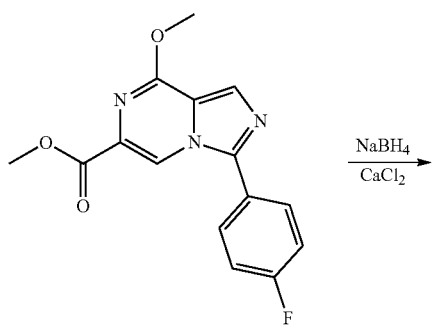

A mixture of powered anhydrous CaCl$_2$ (4.23 g, 38.15 mmol) and NaBH$_4$ (2.86 g, 76.3 mmol) in THF (100 mL) was stirred at room temperature for 1 hour. A solution of compound 19 (2.3 g, 7.63 mmol) in THF (25 mL) was added and then MeOH (25 mL) was added. The reaction mixture was stirred at room temperature for 1.5 hours. The mixture reaction was quenched with water (50 mL). After removing the organic solvent under reduced pressure, the resulting solution was dissolved in EtOAc (200 mL) and water (50 mL). The separated aqueous phase was extracted with EtOAc (3×100 mL). Then the combined organic phases were concentrated under reduced pressure. The residue was purified by column chromatography on silica gel (eluted with PE/EtOAc=2:1) to afford the desired product compound 20 (1.93, 93% yield) as a solid.

$^1$H NMR (400 MHz, CDCl$_3$): δ 7.81 (s, 1H), 7.79-7.74 (m, 3H), 7.25-7.22 (m, 2H), 4.56 (d, J=4.4 Hz, 2H), 4.11 (s, 3H), 2.41 (t, J=4.4 Hz, 1H). MS Calcd.: 273; MS Found: 274([M+H]$^+$).

Synthesis of 6-Chloromethyl-3-(4-fluoro-phenyl)-8-methoxy-imidazo[1,5-a]pyrazine (21)

To a solution of 20 (1.88 g, 6.88 mmol) in dichloromethane (100 mL) was added dropwise thionyl chloride (4.5 mL) while cooling on an ice-water bath. After the addition, the mixture was stirred for another 2 hours. The reaction mixture was quenched with ice-water, washed with brine (20 mL), dried over Na$_2$SO$_4$ and concentrated in vacuo to afford 21 (2.01 g, 100% yield) as a solid.

$^1$H NMR (400 MHz, CDCl$_3$): δ 7.87 (s, 1 H), 7.83-7.79 (m, 3 H), 7.30-7.27 (m, 2 H), 4.50 (s, 2 H), 4.12 (s, 3 H). MS Calcd.: 291; MS Found: 292([M+H]$^+$).

Synthesis of 6-Chloromethyl-3-(4-fluoro-phenyl)-7H-imidazo[1,5-a]pyrazin-8-one (22)

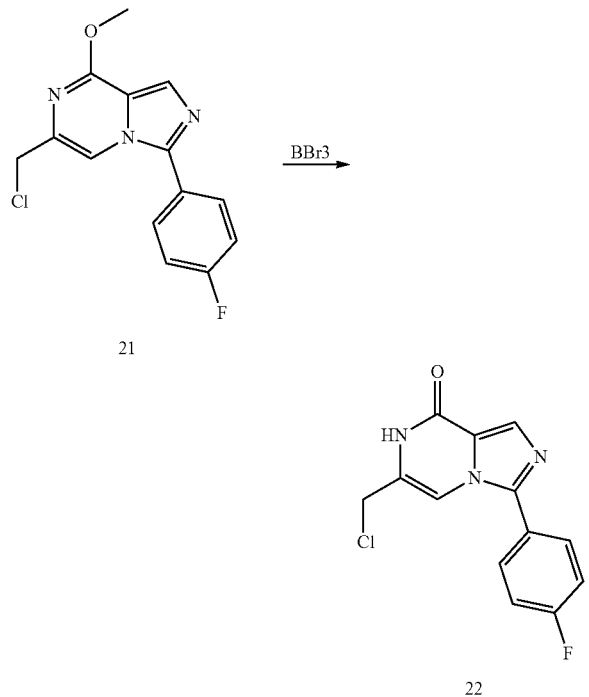

To a solution of 21 (1.87 g, 6.41 mmol) in MeOH (50 mL) was added 6N aqueous HCl and the resulting solution was stirred at 70° C. for one hour. The mixture was concentrated to afford the product 22 (1.60 g, 90% yield) as a white solid.

$^1$H NMR (300 MHz, DMSO-d6): δ 11.29 (s, 1 H), 8.07 (s, 1 H), 7.83-7.87 (m, 2 H), 7.74 (s, 1 H), 7.46-7.50 (m, 2 H), 4.59 (s, 2 H). MS Calcd.: 277; MS Found: 278([M+H]$^+$).

Synthesis of 4-(Azetidin-3-yloxy)-pyridine hydrochloride salt (5)

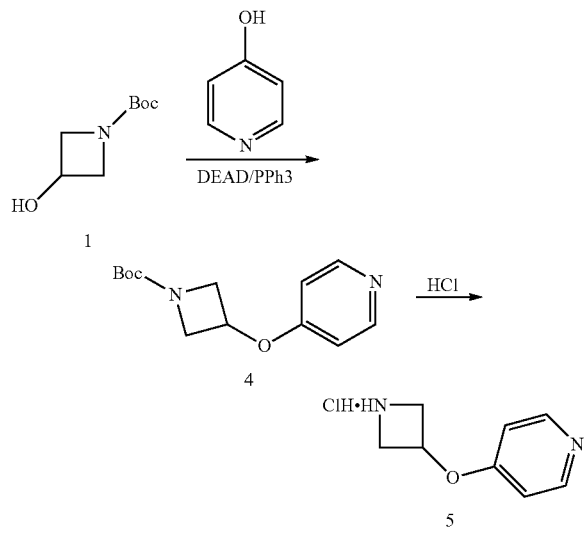

To a solution of tert-butyl 3-hydroxyazetidine-1-carboxylate 1 (4.55 g, 26.3 mmol) in THF (100 mL) was added pyridin-4-ol (2.0 g, 21.0 mmol), PPh$_3$ (6.89 g, 26.3 mmol) and DEAD (4.57 g, 26.3 mmol). The resulting reaction mixture was stirred at 70° C. overnight. TLC indicated that the reaction was complete. The reaction mixture was concentrated in vacuum. The resulting oil was dissolved in 1.0 M aqueous HCl solution (20 mL) and extracted with DCM (50 mL×3), The combined organic phases were washed with HCl (aq) solution (0.5 M, 150 mL). The aqueous fractions were combined and basified to pH≈12 using NaOH (1.0 M) and extracted with DCM (100 mL×3). The combined organic phases were dried over anhydrous Na$_2$SO$_4$, filtered and concentrated in vacuum. The residue was purified by column chromatography on silica gel to afford to afford 4 (2.81 g, 53% yield) as a solid.

$^1$HNMR (400 MHz, DMSO-d6): δ 8.41 (d, J=6.0 Hz, 2 H), 6.88 (d, J=6.0 Hz, 2 H), 5.07-5.09 (m, 1 H), 4.32-4.33 (m, 2 H), 3.80-3.82 (m, 2 H), 1.39 (s, 9 H). MS Calcd.: 250; MS Found: 251 ([M+H]$^+$).

To a solution of 4 (2.81 g, 11.2 mmol) in Et$_2$O (100 mL) was added HCl in Et$_2$O (20 mL). The resulting reaction mixture was stirred at room temperature overnight. TLC indicated that the reaction was complete. The reaction mixture was filtered and the solid was dried to afford 5 (1.82 g, 87% yield).

$^1$HNMR (300 MHz, DMSO-d6): δ 9.58 (s, 2 H), 8.77-8.79 (m, 2 H), 7.48-7.49 (m, 2 H), 5.40-5.45 (m, 1 H), 4.49-4.51 (m, 2 H), 4.07-4.11 (m, 2 H). MS Calcd.: 150; MS Found: 151 ([M+H]$^+$).

Synthesis of 3-(4-fluorophenyl)-6-((3-(pyridin-4-yloxy)azetidin-1-yl)methyl)imidazo[1,5-a]pyrazin-8(7H)-one (P1)

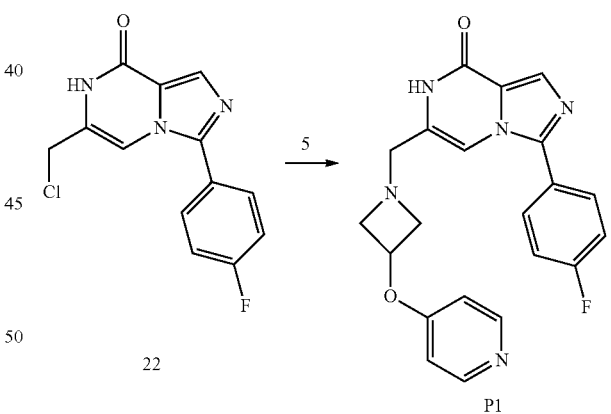

To a mixture of compound 22 (1.5 g, 5.4 mmol) and 5 (1.31 g, 7.0 mmol) in MeCN (100 mL) was added DIPEA (6.96 g, 5.4 mmol). The reaction mixture was heated and refluxed overnight. The solvent was removed in vacuum. The residue was purified by flash column chromatography on reverse phase silica gel (eluted by 5%~95% MeCN in water) to afford desired product P1 (1.28 g, 62% yield) as a solid.

$^1$H NMR (400 MHz, DMSO-d6): δ 10.7 (s, 1H), 8.37 (d, J=6.0 Hz, 2H), 7.85 (s, 1H), 7.85-7.82 (m, 2H), 7.42 (m, 2H), 7.34 (s, 1H), 6.86 (d, J=6.0 Hz, 2H), 4.93 (m, 1H), 3.88-3.77 (m, 2H), 3.42 (s, 2H), 3.18-3.14 (m, 2H). MS Calcd.: 391; MS Found: 392 ([M+H]$^+$).

Synthesis of (6-Methoxy-5-{[(tetrahydro-pyran-4-carbonyl)-amino]-methyl}-pyrazin-2-yl)-carbamic acid tert-butyl ester (23)

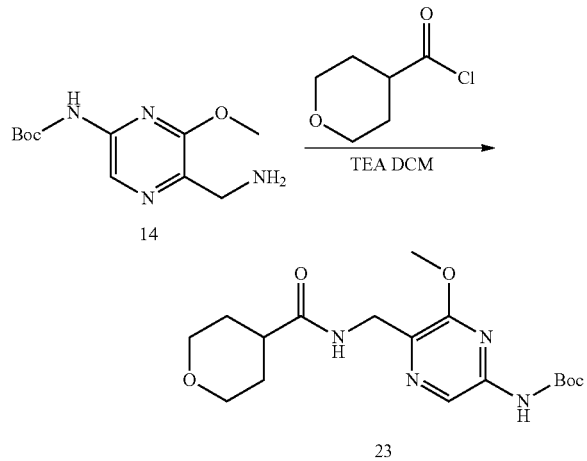

To a solution of compound 14 (28.4 g, 0.11 mol) in DCM (200 mL) was added TEA (49 mL, 0.34 mol), then tetrahydropyran-4-carbonyl chloride (17.5 g, 0.13 mol) was added dropwise. The resulting reaction mixture was stirred at room temperature overnight. TLC indicated that the reaction was complete. The reaction was quenched with water (100 mL). The organic phase was separated and the aqueous phase was extracted with DCM (200 mL×2). The combined organic phases were dried over anhydrous $Na_2SO_4$, filtered and concentrated in vacuum. The residue was purified by column chromatography on silica gel (PE/EA=5/1 to 1/3) to afford 23 (31 g, 75% yield) as a solid.

$^1$H NMR (DMSO-d6, 400 MHz): δ 9.89 (s, 1H), 8.47 (s, 1H), 8.10-8.07 (t, J=5.2 Hz, 1H), 4.29-4.28 (d, J=5.2 Hz, 2H), 3.87 (s, 3H), 3.85-3.82 (m, 2H), 3.32-3.25 (m, 2H), 2.45-2.43 (m, 1H), 1.60-1.55 (m, 4H), 1.48 (s, 9H). MS Calcd.: 366; MS Found: 367 ([M+H]$^+$).

Synthesis of Tetrahydro-pyran-4-carboxylic acid (5-amino-3-methoxy-pyrazin-2-ylmethyl)-amide (24)

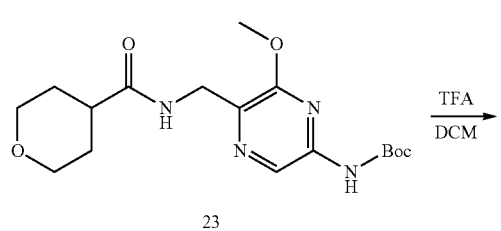

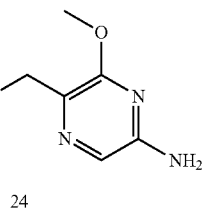

Compound 23 (19.0 g, 0.08 mol) was dissolved in DCM (100 mL). TFA (100 mL) was added. The reaction was stirred at room temperature overnight. TLC indicated that the reaction was complete. The solvent was removed. The residue was diluted with DCM (100 mL) and saturated $NaHCO_3$ aqueous solution (100 mL). The aqueous phase was extracted with DCM (100 mL×2). The combined organic phases were dried over anhydrous $Na_2SO_4$, filtered and concentrated in vacuum. The residue was purified by column chromatography on silica gel (PE/EA=6/1 to 1/1) to afford 24 (19 g, 85% yield) as a solid.

$^1$H NMR (DMSO-d6, 400 MHz): δ 7.87 (t, J=4.8 Hz, 1H), 7.36 (s, 1H), 6.26 (br. s, 2H), 4.16 (d, J=4.8 Hz, 2H), 3.86-3.82 (m, 2H), 3.80 (s, 3H), 3.30-3.24 (m, 2H), 2.41 (m, 1H), 1.59-1.54 (m, 4H). MS Calcd.: 266; MS Found: 267 ([M+H]$^+$).

Synthesis of Tetrahydropyran-4-carboxylic acid (5-iodo-3-methoxy-pyrazin-2-ylmethyl)-amide (25)

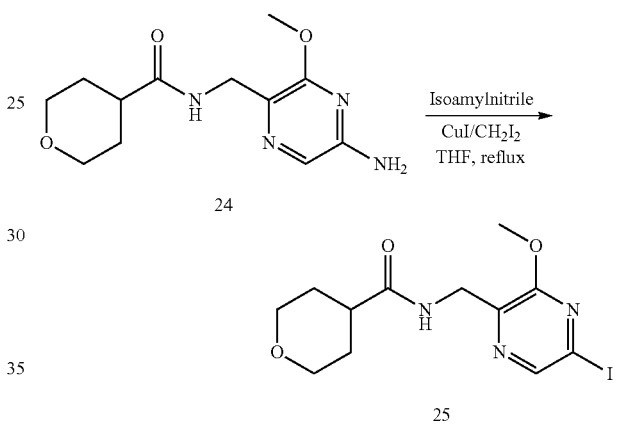

To a mixture of compound 24 (15.5 g, 58.4 mmol), $CH_2I_2$ (23.5, 87.6 mmol) and isoamyl nitrite (23.9 g, 204 mmol) in THF (600 mL) was added CuI (11.3 g, 39.6 mmol) under an $N_2$ atmosphere. The reaction mixture was stirred at 80° C. for 7 hours. The precipitate was filtered. The filtrate was concentrated and purified by column chromatography (MeOH/DCM=1/20) to get crude product, then purified by flash column chromatography on reverse phase silica gel (eluted by 5%~95% MeCN in water) to afford desired product compound 25 (4.5 g, 20% yield) as a solid.

$^1$H NMR (DMSO-d6, 300 MHz): δ 8.41 (s, 1H), 8.16 (t, J=5.4 Hz, 1H), 4.28 (d, J=5.4 Hz, 2H), 3.92 (s, 3H), 3.87-3.81 (m, 2H), 3.30-3.24 (m, 2H), 2.49 (m, 1H), 1.60-1.56 (m, 4H). MS Calcd.: 377 MS Found: 378 ([M+H]$^+$).

Synthesis of 6-Iodo-8-methoxy-3-(tetrahydro-pyran-4-yl)-imidazo[1,5-a]pyrazine (26)

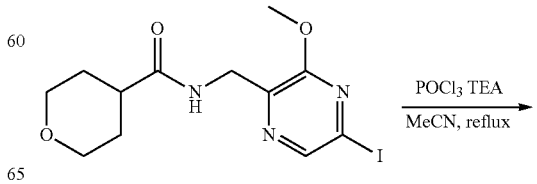

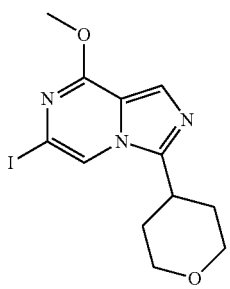

26

To a solution of compound 25 (4.5 g, 16.9 mmol) in MeCN (100 mL) was added POCl₃ (18 g, 118 mmol). The reaction was stirred at reflux overnight under an N₂ atmosphere. The solvent was removed under reduced pressure. The residue was treated with ice water (30 mL) and DCM (150 mL). The pH was adjusted to 7~8 by saturated Na₂CO₃ solution. The separated aqueous phase was extracted with DCM (100 mL×4). The combined organic phases were concentrated under reduced pressure to afford desired 26 (4.2 g, 99% yield) as a solid.

$^1$H NMR (DMSO-d6, 400 MHz): δ 8.46 (s, 1H), 7.64 (s, 1H), 3.98 (s, 3H), 3.94 (m, 2H), 3.53-3.47 (m, 3H), 1.81-1.77 (m, 4H). MS Calcd.: 359; MS Found: 360 ([M+H]⁺).

Synthesis of 8-Methoxy-3-(tetrahydro-pyran-4-yl)-imidazo[1,5-a]pyrazine-6-carboxylic acid methyl ester (27)

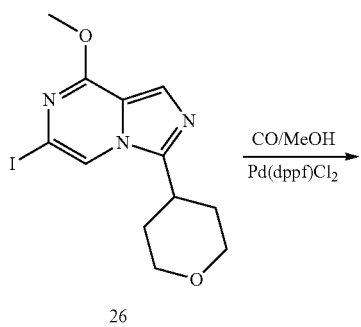

26

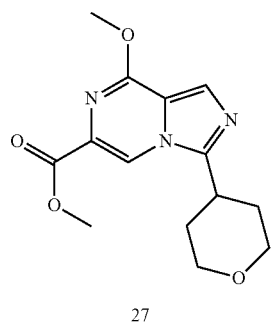

27

To a suspension of compound 26 (4.2 g, 11.7 mmol) in MeOH (100 mL) was added CuI (0.7 g, 3.0 mmol), Pd(dppf)₂Cl₂ (1.0 g, 1.17 mmol) and TEA (16 mL). The reaction mixture was stirred on an oil bath set at 85° C. for 16 hours under a CO atmosphere (3 MPa). The precipitate was filtered and the filtrate was evaporated under reduced pressure. The residue was purified by column chromatography (eluted by EtOAc/PE=2/1 to MeOH/DCM=1/20) to afford desired 27 (2.7 g, 80% yield) as a solid.

$^1$H NMR (CDCl₃, 400 MHz): δ 8.32 (s, 1H), 7.70 (s, 1H), 4.17 (s, 3H), 4.14 (m, 2H), 3.98 (s, 3H), 3.66-3.60 (m, 2H), 3.31-3.26 (m, 1H), 2.17-2.13 (m, 2H), 1.93 (m, 2H). MS Calcd.: 291; MS Found: 292 ([M+H]⁺).

Synthesis of [8-Methoxy-3-(tetrahydro-pyran-4-yl)-imidazo[1,5-a]pyrazin-6-yl]-methanol (28)

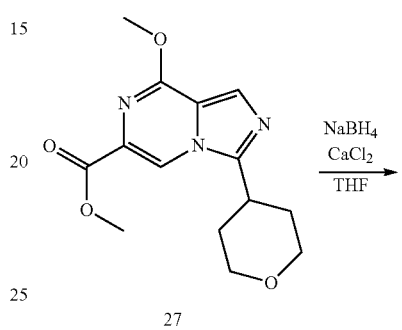

27

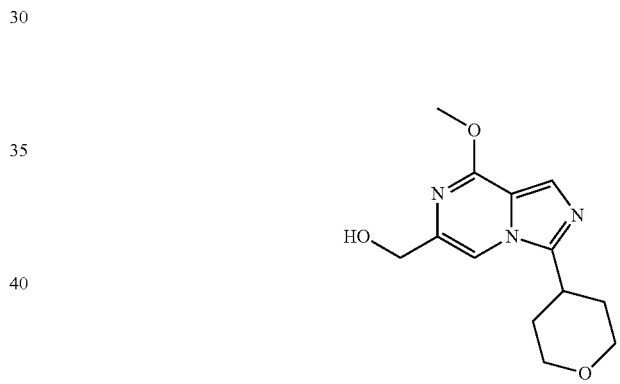

28

A mixture of powered anhydrous CaCl₂ (2.4 g, 21.5 mmol) and NaBH₄ (1.6 g, 42.9 mmol) was stirred in THF (100 mL) for 1 hour at rt. A solution of compound 27 (2.4 g, 4.29 mmol) in THF (25 mL) was added and then MeOH (25 mL) was added. The reaction mixture was stirred at room temperature for 1.5 hours. The mixture reaction was quenched with water (50 mL). After removing the organic solvent under reduced pressure, the residue was partitioned between EtOAc (200 mL) and water (50 mL). The separated aqueous phase was extracted with EtOAc (100×3 mL). Then the combined organic phases were concentrated under reduced pressure. The residue was purified by column chromatography on silica gel (eluted by DCM/MeOH=100/1 to 30/1) to afford the desired product compound 28 as a solid (1.87, 80% yield).

$^1$H NMR (CDCl₃, 400 MHz): δ 7.65 (s, 1H), 7.43 (s, 1H), 4.58 (s, 2H), 4.13 (d, J=12.0 Hz, 2H), 4.07 (s, 3H), 3.60 (dd, J=10.4 Hz, 10.8 Hz, 2H), 3.24-3.17 (m, 1H), 2.60 (m, 1H), 2.18-2.06 (m, 2H), 1.90 (d, J=12.8 Hz, 2H). MS Calcd.: 263; MS Found: 264 ([M+H]⁺).

37

Synthesis of 6-Chloromethyl-3-(tetrahydropyran-4-yl)-7H-imidazo[1,5-a]pyrazin-8-one (30)

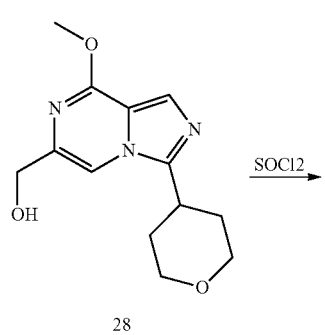

To a solution of compound 28 (1.9 g, 7.11 mmol) in DCM (100 mL) was added SOCl$_2$ (5 mL) at 0° C., then the reaction mixture was stirred at room temperature for 5 hours. TLC and LC-MS showed that the starting martial had been consumed. Then the mixture solution was concentrated and the residue was dissolved in HCl (aq.) solution (6N, 20 mL). The mixture reaction was stirred at room temperature for 10 minutes. The reaction mixture was then concentrated under reduced pressure to afford the desired product compound 29 (1.90 g, 95% yield) as a solid.

$^1$H NMR (DMSO-d6, 300 MHz): δ 11.49 (s, 1H), 8.28 (s, 1H), 8.00 (s, 1H), 4.55 (s, 2H), 3.97 (dd, J=2.4 Hz, 2.8 Hz, 2H), 3.53-3.43 (m, 3H), 1.95-1.81 (m, 4H). MS Calcd.: 267 MS Found: 268 ([M+H]$^+$).

38

Synthesis of 3-(azetidin-3-yloxy)-pyridine hydrochloride (7)

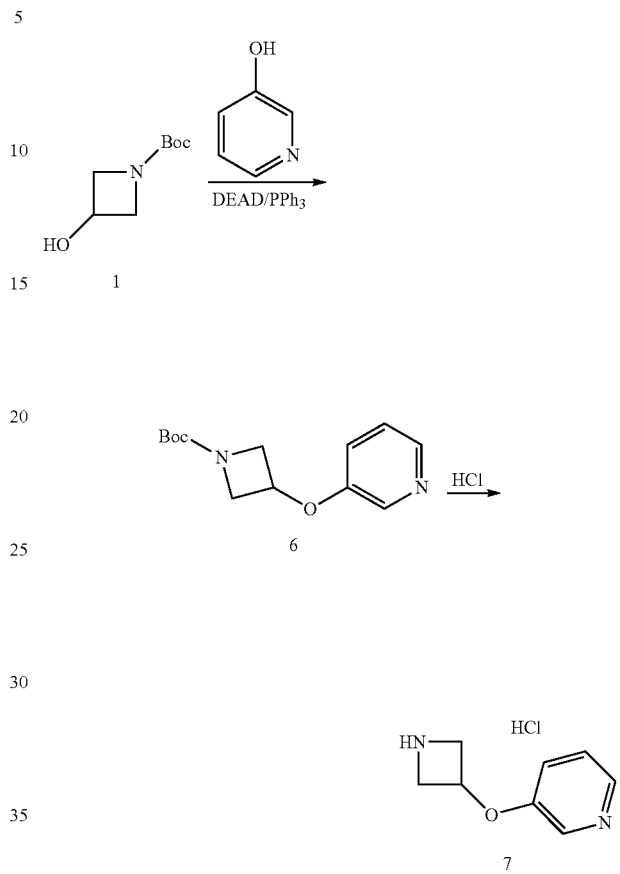

Compound 7 was prepared by a similar procedure to the one employed for the preparation of amine 5.

Analytical data for 7: $^1$H NMR ((DMSO-d$_6$, 400 MHz): δ 9.73 (br d, 2H), 8.55 (d, J=2.4 Hz, 2H), 8.47 (d, J=4.4 Hz, 2H), 7.88-7.75 (m, 2H), 5.28 (t, J=5.6 Hz, 1H), 4.50-4.43 (m, 2H), 4.08-4.00 (m, 2H). MS Calcd.: 150, MS Found: 151 ([M+H]$^+$).

Synthesis of 6-[3-(pyridin-3-yloxy)-azetidin-1-ylmethyl]-3-(tetrahydropyran-4-yl)-7H-imidazo[1,5-a]pyrazin-8-one (P2)

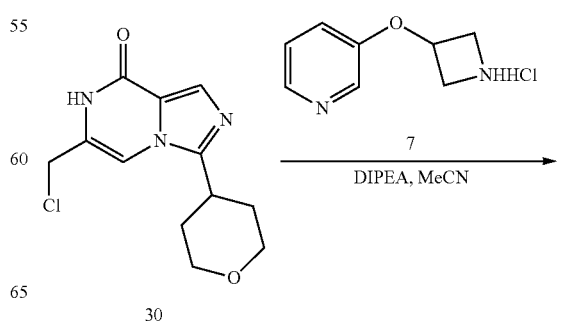

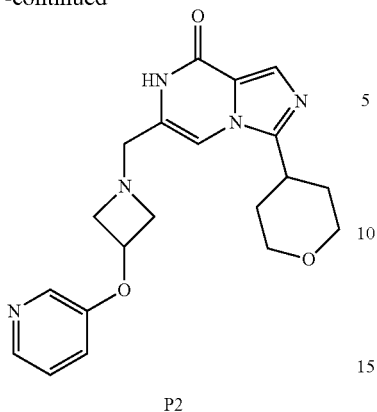

P2

To a mixture of compound 30 (550 mg, 2.05 mmol) and 7 (500 mg, 2.67 mmol) in MeCN (200 mL) was added DIPEA (2.7 g, 20.5 mmol). The reaction mixture was refluxed overnight. The solvent was removed in vacuum. The crude product was purified by flash column chromatography on reverse phase silica gel (eluted by 5%~95% MeCN in water) to afford desired product P2 (360 mg, 46% yield) as a solid.

$^1$H NMR (CDCl$_3$, 300 MHz): δ 8.26 (d, J=4.0 Hz 1H), 8.22 (s, 1H), 8.20 (d, J=2.8 Hz, 1H), 7.91 (s, 1H), 7.24-7.21 (m, 1H), 7.07 (d, J=2.8 Hz, 1H), 6.79 (s, 1H), 4.86 (m, 1H), 4.13 (m, 2H), 3.89 (t, J=7.6 Hz, 2H), 3.57 (m, 2H), 3.50 (s, 2H), 3.28 (dd, J=2.4 Hz, 6.8 Hz, 2H), 3.10-30.6 (m, 1H), 2.14-2.08 (m, 2H), 1.87 (m, 2H). MS Calcd.: 381; MS Found: 382 ([M+H]$^+$).

Synthesis of 3H-imidazole-4-carboxylic acid methyl ester (32)

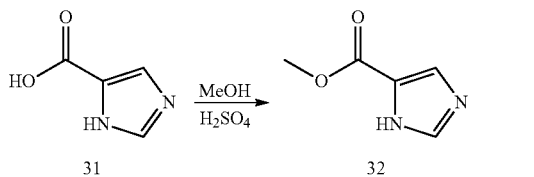

To a solution of compound 31 (25 g, 0.22 mol) in MeOH (300 mL) was added H$_2$SO$_4$ (24 mL). The mixture was stirred at reflux for 18 hours. Then pH of the reaction solution was adjusted to ~7. The reaction mixture was concentrated in vacuo. The residue was dissolved in 100 ml of MeOH and stirred at room temperature for 15 minutes. The mixture solution was filtered and the filtrate was concentrated to afford the crude 32 (28 g, 100% yield) as a solid, which was used for next step without further purification.

$^1$H NMR (400 MHz, DMSO-d$_6$): δ 7.80 (s, 2H), 3.57 (s, 3H).

Synthesis of 3H-imidazole-4-carboxylic acid methyl ester (33)

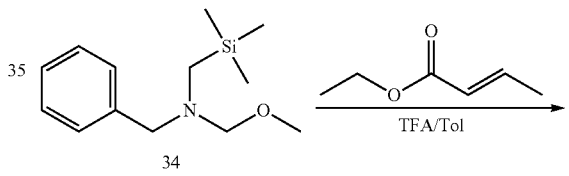

To a solution of compound 32 (22 g, 0.18 mol) in MeCN (500 mL) was added NBS (66 g, 0.37 mol). The mixture was stirred at 70° C. for 4 hours. The reaction mixture was concentrated in vacuo. The crude product was purified by column chromatography on silica gel (eluting with PE/EtOAc=5:1 to 1:1) to afford compound 33 (20 g, 40% yield) as a solid.

$^1$H NMR (400 MHz, DMSO-d$_6$): δ 14.35 (br, 1H), 3.81 (s, 3H).

Synthesis of racemic trans-1-benzyl-4-methyl-pyrrolidine-3-carboxylic acid ethyl ester (35)

To a solution of 34 (69 g, 0.29 mol) in toluene was added but-2-enoic acid ethyl ester (50 g, 0.44 mol) and TFA (25 mL, 0.32 mol). The resulting solution was stirred at 50° C. under N$_2$ overnight. To the reaction mixture was added saturated aqueousNaHCO$_3$ solution (300 mL), and the aqueous phase was extracted with EtOAc (500 mL×3). The combined organic layers were washed with brine (300 mL), dried over Na$_2$SO$_4$, filtered and concentrated in vacuo. The crude product was purified by flash chromatography (PE/EA=20:1 to 6:1) to afford the desired racemic trans product 35 (41 g, 57% yield) as an oil.

Synthesis of (S,S)-trans-1-benzyl-4-methyl-pyrrolidine-3-carboxylic acid ethyl ester (S,S)-(35)

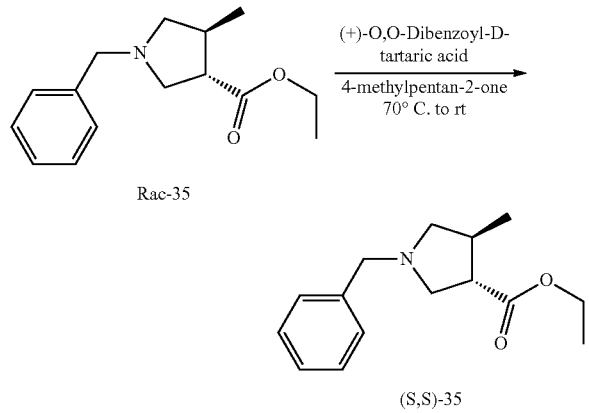

Rac-35

(S,S)-35

To a solution of Rac-35 (37 g, 0.15 mol) in 4-methyl-2-pentanone was added (−)-dibenzoyl-L-tartaric acid (34.78 g, 0.65 eq.) and the resulting reaction mixture was heated to 72° C. for 1 hr after which it was allowed to cool to RT where it was maintained for 4 hrs. The resulting solid was filtered off and the filtrate was washed with conc. aq. sodium carbonate (55 mL). The aqueous phase was extracted with 4-methyl-2-pentanone (15 mL) and the combined organic phases were washed with brine (40 mL). The organic phase was then treated with (+)-dibenzoyl-D-tartaric acid (32.16 g) and heated to 72° C. for 1 hr. The reaction mixture was cooled to RT and maintained at this temperature for 4 hrs. The solid was filtered off and dried on the filter. The solid was then recrystallized by adding a mixture of MTBE-MeOH (2:1, 270 mL), heating to 70° C. for 1 hr and allowing the product to precipitate at RT for 4 hrs. The resulting solid was filtered off, washed with MTBE and dried. Two more recrystallization following the same procedure afforded the pure product as a (+)-dibenzoyl-D-tartaric acid salt (>98% ee with based on the isolated free base).

The free base was liberated by the following procedure: the filtered solid was partitioned between MTBE (250 mL) and conc. aq. sodium carbonate (250 mL) and the aqueous phase was extracted with MTBE (125 mL). The combined organic phases were washed with water (250 mL) and brine (50 mL) and evaporated to give the product as a clear oil (13.79 g, 0.056 mol) as a clear oil.

Synthesis of racemic trans-4-methyl-pyrrolidine-1,3-dicarboxylic acid 1-tert-butyl ester 3-methyl ester rac-(36)

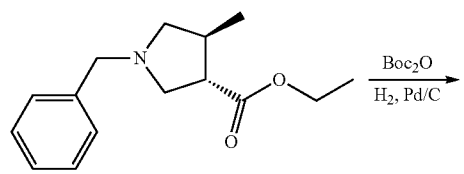

35

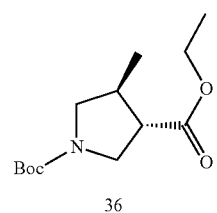

36

To a solution of 35 (41 g, 0.17 mol) and Boc₂O (43 g, 0.20 mol) in EtOH (500 mL) was added Pd/C (5%, 10.0 g). The reaction mixture was stirred at 50° C. for 48 hours under an atmosphere of H₂ (50 Psi). The reaction mixture was filtered and concentrated in vacuo. The crude product was purified by flash chromatography (PE/EA=20/1) to afford the desired racemic trans 36 (20 g, 46% yield) as an oil.

Synthesis of (S,S)-trans-4-methyl-pyrrolidine-1,3-dicarboxylic acid 1-tert-butyl ester (S,S)-(37) via (S,S)-trans-4-methyl-pyrrolidine-1,3-dicarboxylic acid 1-tert-butyl ester 3-methyl ester (S,S)-(36)

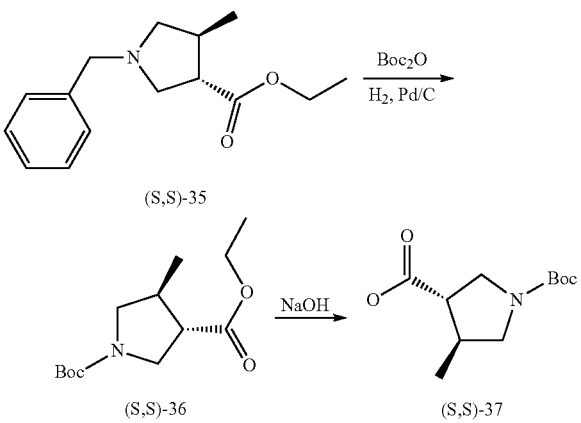

(S,S)-35

(S,S)-36

(S,S)-37

A solution of (S,S)-35 (12.80 g, 51.8 mmol) and Boc₂O (13.57 g, 1.2 eq) in EtOH (150 mL) was placed in an autoclave under N₂-protective atmosphere and Pd/C (5%, 2.56 g) was added. The reaction mixture was hydrogenated with stirring at 45-50° C. at 15-20 Bar H₂ pressure until no more hydrogen was absorbed (48 hrs). The reaction mixture was cooled to RT and filtered, and the filter was washed with EtOH (50 mL). The filtrate was evaporated at <45° C. to about 25 mL. Water (10 mL) and NaOH solution (2 mL) was added and the resulting reaction mixture was stirred at RT for 2 hrs (GC analysis showed complete disappearance of the starting material at this point). Water (125 mL) was added and the resulting mixture was extracted with MTBE (2×50 mL). The aqueous phase was treated with 2N HCl solution to achieve a pH value of 3-4 (ca. 25 mL) and the resulting solution was extracted with MTBE (2×150 mL). The combined organic extracts were washed with brine (50 mL) and evaporated to about 20 mL. n-Heptane (40 mL) was added and the resulting reaction mixture was left at 0° C. for 2 hrs after which the solid was filtered off and dried to give the product (S,S)-37 as a solid (9.48 g, 41.7 mmol). The ee at this step was determined to 97.5%. This material had identical NMR and LC/MS properties to rac-37 described below.

Synthesis of (S,S)-trans-4-methyl-pyrrolidine-1,3-dicarboxylic acid 1-tert-butyl ester (S,S)-(37) via (S,S)-trans-4-methyl-pyrrolidine-1,3-dicarboxylic acid 1-tert-butyl ester 3-methyl ester (S,S)-(36)

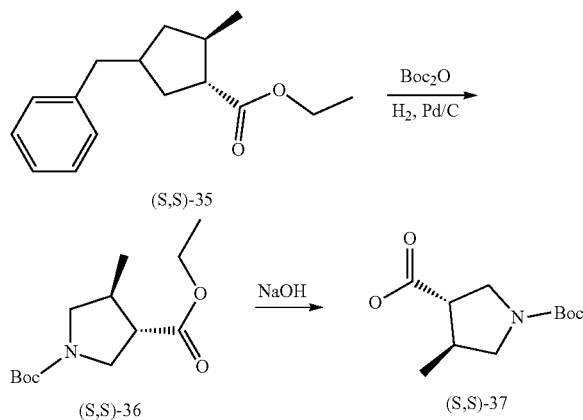

A solution of (S,S)-35 (12.80 g, 51.8 mmol) and Boc$_2$O (13.57 g, 1.2 eq) in EtOH (150 mL) was placed in an autoclave under N$_2$-protective atmosphere and Pd/C (5%, 2.56 g) was added. The reaction mixture was hydrogenated with stirring at 45-50° C. at 15-20 Bar H$_2$ pressure until no more hydrogen was absorbed (48 hrs). The reaction mixture was cooled to RT and filtered, and the filter was washed with EtOH (50 mL). The filtrate was evaporated at <45° C. to about 25 mL. Water (10 mL) and NaOH solution (2 mL) was added and the resulting reaction mixture was stirred at RT for 2 hrs (GC analysis showed complete disappearance of the starting material at this point). Water (125 mL) was added and the resulting mixture was extracted with MTBE (2×50 mL). The aqueous phase was treated with 2N HCl solution to achieve a pH value of 3-4 (ca. 25 mL) and the resulting solution was extracted with MTBE (2×150 mL). The combined organic extracts were washed with brine (50 mL) and evaporated to about 20 mL. n-Heptane (40 mL) was added and the resulting reaction mixture was left at 0° C. for 2 hrs after which the solid was filtered off and dried to give the product (S,S)-37 as a solid (9.48 g, 41.7 mmol). The ee at this step was determined to 97.5%. This material had identical NMR and LC/MS properties to rac-37 described below.

Synthesis of racemic trans-4-methyl-pyrrolidine-1,3-dicarboxylic acid 1-tert-butyl ester (37)

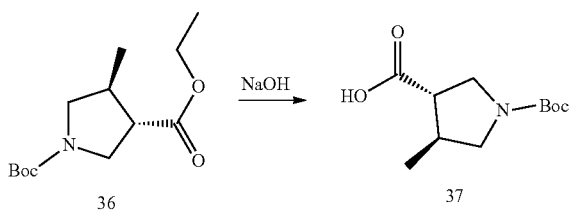

A solution of compound 36 (10.0 g, 39.1 mmol), NaOH (3.10 g, 78.2 mmol) in methanol/H$_2$O (50/5 mL) was stirred at room temperature for 2 hours. The reaction mixture was concentrated and extracted with EA (150 mL). The aqueous phase was acidified by 2 M HCl at 0° C. to pH ~5 and extracted with EtOAc (150 mL×3). The combined organic layers were washed with brine, dried and concentrated to afford compound 37 (8.0 g, 90%) as an oil.

$^1$H NMR (400 MHz, DMSO-d$_6$): δ 12.43 (s, 1H), 3.55-3.51 (m, 2H), 3.47-3.27 (m, 1H), 2.85-2.78 (m, 1H), 2.63-2.57 (m, 1H), 2.34-2.28 (m, 1H), 1.55 (s, 9H), 1.03 (d, J=4.8 Hz, 3H).

Synthesis of (S,S)-trans-3-acetyl-4-methyl-pyrrolidine-1-carboxylic acid tert-butyl ester (S,S)-(39) via (S,S)-trans-3-(methoxy-methyl-carbamoyl)-4-methyl-pyrrolidine-1-carboxylic acid tert-butyl ester (S,S)-(38)

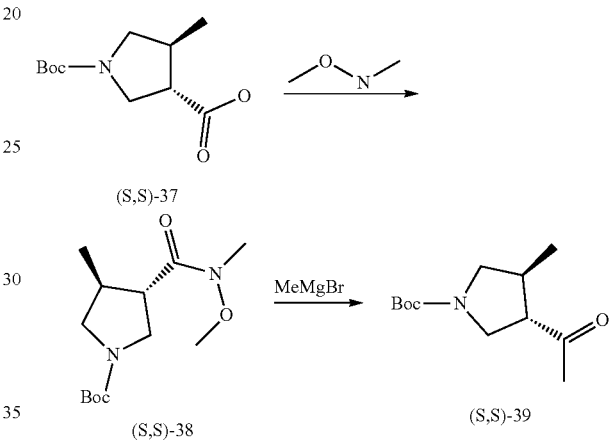

To a solution of (S,S)-37 (5.0 g, 22.0 mmol) in DCM (50 mL) was added CDI (4.25 g, 1.2 eq) over 10 mins while keeping the temperature below 5° C. throughout. The reaction mixture was stirred for 1 hr after which N,O-dimethylhydroxylamine hydrochloride (3.0 g, 1.4 eq) was added in small portions over about 10 mins keeping the temperature below 5° C. The reaction was then allowed to warm to room temperature and stirred for 12 hrs at which the starting material had been fully consumed. Water (50 mL) was added, the phases were separated and the aq phase was extracted with DCM (35 mL). The combined organic phases were washed with water (50 mL) and concentrated to about 5 mL. THF (20 mL) was added and the resulting solution was evaporated to dryness and dried in high vacuum. Dry THF (50 mL) was added, the solution was cooled to 0° C. and MeMgCl (3 M, 11.35 mL, 1.5 eq) was added dropwise under an N$_2$ atmosphere over 30 mins making sure to maintain the temperature below 5° C. The reaction mixture was then heated to RT and stirred for 2 hrs (at this point the Weinreb amide had been completely converted). Saturated aq. ammonium chloride (50 mL) was added dropwise below 25° C. to quench the reaction and the resulting reaction mixture was extracted with EtOAc (2×50 mL), and the combined organic extracts were washed with brine (50 mL) and evaporated to about 5 mL. THF (25 mL) was added and the resulting solution was evaporated to dryness in vacuo to give the product (S,S)-39 as an oil (4.91 g, 21.6 mmol) in about 98% ee. All spectral properties were identical to those of rac-39.

Synthesis of racemic trans-3-(methoxy-methyl-carbamoyl)-4-methyl-pyrrolidine-1-carboxylic acid tert-butyl ester (38)

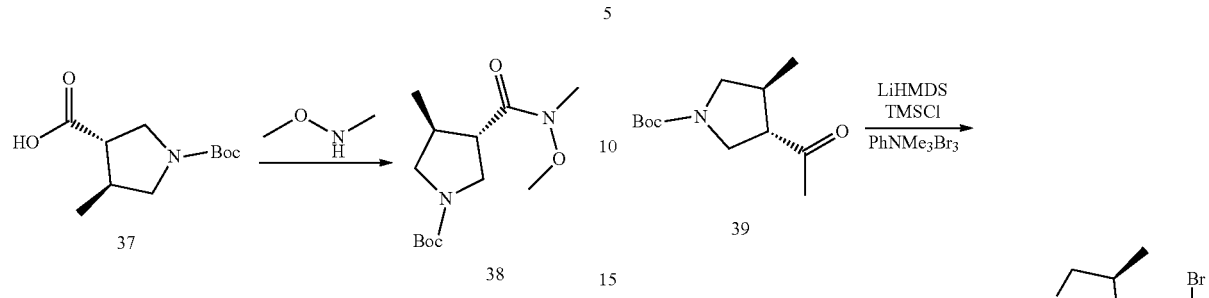

To a solution of 37 (8.0 g, 34.9 mmol) and O,N-dimethylhydroxylamine (4.0 g, 41.9 mmol) in DCM (50 mL) was added CDI (6.8 g, 41.9 mmol). The mixture reaction was stirred at 20° C. for 18 hours. To the mixture solution was added water (100 mL) and extracted with DCM (100 mL×3). The combined organic layers were washed with brine (30 mL), dried and concentrated in vacuo. The crude product was purified by flash chromatography (PE/EtOAc=20/1) to afford racemic trans 38 (8.0 g, 84% yield) as an oil.

$^1$H NMR (400 MHz, DMSO-$d_6$): δ 3.68 (s, 3H), 3.60-3.48 (m, 2H), 3.20-3.05 (m, 5H), 2.84-2.73 (m, 1H), 2.40-2.32 (m, 1H), 1.39 (s, 9H), 0.96 (d, J=4.8 Hz, 3H).

Synthesis of racemic trans-3-acetyl-4-methyl-pyrrolidine-1-carboxylic acid tert-butyl ester (39)

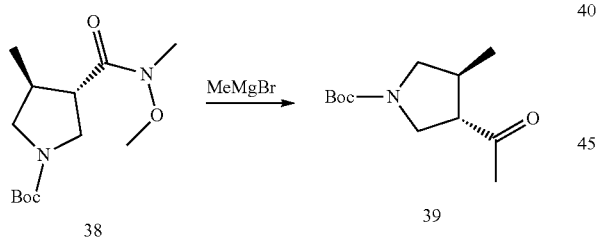

To a solution of 38 (8.0 g, 29.4 mmol) in THF (60 mL) was added MeMgBr (3.0 M, 13 mL, 38.2 mmol) at 0° C. The reaction mixture was stirred at room temperature for 2 hours. The mixture reaction was quenched with saturated NH$_4$Cl aqueous solution (200 mL) and extracted with EtOAc (300 mL×3). The combined organic layers were washed with brine, dried and concentrated in vacuo. The crude product was purified by flash chromatography (PE/EtOAc=10/1) to afford the desired racemic trans 39 (6.0 g, 94% yield) as an oil.

$^1$H NMR (400 MHz, DMSO-$d_6$): δ 3.66-3.51 (m, 1H), 3.49-3.39 (m, 1H), 3.34-3.24 (m, 1H), 2.88-2.79 (m, 2H), 2.34-2.30 (m, 1H), 2.15 (s, 3H), 1.36 (s, 9H), 1.02-1.00 (m, 3H).

Synthesis racemic trans-3-(2-bromo-acetyl)-4-methyl-pyrrolidine-1-carboxylic acid tert-butyl ester (40)

A solution of LiHMDS (1M in THF, 40 mL, 40 mmol) was added to the solution of 39 (6.0 g, 26.4 mmol) in THF (100 mL) under an N$_2$ atmosphere at −78° C. The reaction mixture was stirred at this temperature for one hour. Then TMSCl (10 mL, 26.4 mmol) was added dropwise at −78° C. and the reaction temperature was raised to 0° C. After one hour, PhMe$_3$NBr$_3$ (11.0 g, 29.1 mmol) was added at 0° C. The mixture reaction was stirred for another an hour, then stirred at room temperature overnight. The reaction was quenched with water (200 mL) and extracted with EtOAc (250 mL×3). The combined organic layers were washed with brine, dried and concentrated in vacuo. The crude product was purified by flash chromatography (PE/EtOAc=10/1) to afford the desired racemic trans 40 (4.5 g, 56% yield) as an oil.

$^1$H NMR (400 MHz, CDCl$_3$): δ 4.05 (s, 2H), 3.69-3.50 (m, 2H), 3.36-3.30 (m, 1H), 3.04-2.86 (m, 2H), 2.51-2.43 (m, 1H), 1.39 (s, 9H), 1.10-1.05 (m, 3H).

Synthesis (S,S)-trans-3-(2-bromo-acetyl)-4-methyl-pyrrolidine-1-carboxylic acid tert-butyl ester (S,S)-(40)

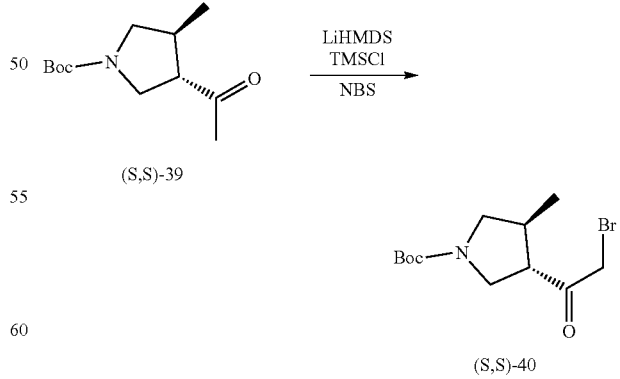

A solution of LiHMDS (1M in THF, 21.12 mL, 21.12 mmol) was added dropwise to a solution of (S,S)-39 (3.96 g, 17.4 mmol) in THF (50 mL) under an N$_2$ atmosphere at −78° C. The reaction mixture was stirred at this temperature for one hour. Then TMSBr (6.43 g, 42 mmol) was added dropwise at −78° C. and the reaction temperature was allowed to warm to 0° C. After one hour NBS (2.76 g, 15.5 mmol) was added in small portions at 0° C. TLC showed that all starting material had been consumed. Water (20 mL) was added dropwise keeping the temperature at RT and the resulting reaction mixture was stirred for 30 mins. The phases were separated and the aq phase was extracted with MTBE (2×15 mL). The combined organic phases were washed with brine, dried and concentrated in vacuo. The residue was redissolved in MTBE (25 mL), washed with water (3×10 mL) and brine (10 mL), and concentrated in vacuo to give the product as an oil which could be purified by flash chromatography (PE/EtOAc=10/1) to afford the desired (S,S)-40 (6.4 g, 20.9 mmol) as an oil.

Synthesis of racemic trans-2,5-dibromo-3-[2-(1-tert-butoxycarbonyl-4-methyl-pyrrolidin-3-yl)-2-oxo-ethyl]-3H-imidazole-4-carboxylic acid methyl ester (41)

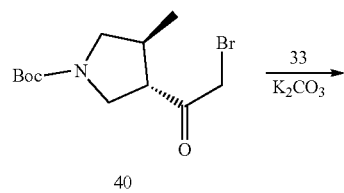

40

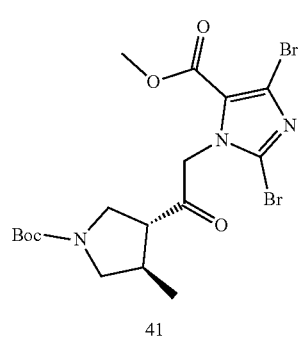

41

To a solution of 33 (4.1 g, 14.7 mmol) in DMF (30 mL) was added K₂CO₃ (5.8 g, 42.5 mmol). After stirring for 15 minutes, compound 40 (4.5 g, 14.7 mmol) was added to the reaction mixture. The reaction was stirred at room temperature for 5 hours. The reaction mixture was diluted with EtOAc (200 mL), washed with brine (200 mL×2). Then the organic phase was dried (Na₂SO₄), filtered and concentrated in vacuo. The residue was purified by column chromatography (PE/EtOAc=10/0~3/1) to afford racemic trans 41 (3.0 g, 40% yield) as a solid.

¹H NMR (400 MHz, DMSO-d₆): δ 5.41 (s, 2H), 3.78 (s, 3H), 3.68-3.66 (m, 1H), 3.48-3.45 (m, 1H), 3.34-3.31 (m, 1H), 3.20-3.25 (m, 1H), 2.92-2.87 (m, 1H), 2.50-2.46 (m, 1H), 1.36 (s, 9H), 1.07 (m, 3H).

Synthesis of (S,S)-trans-2,5-dibromo-3-[2-(1-tert-butoxycarbonyl-4-methyl-pyrrolidin-3-yl)-2-oxo-ethyl]-3H-imidazole-4-carboxylic acid methyl ester (S,S)-(41)

(S,S)-40

(S,S)-41

To a solution of 33 (2.78 g, 9.79 mmol) in NMP (30 mL) was added Na₂CO₃ (3.11 g, 26.2 mmol). After stirring for 15 minutes, compound (S,S)-40 (4.5 g, 14.7 mmol) was added to the reaction mixture. The reaction was stirred at room temperature for 5 hours. The reaction mixture was diluted with EtOAc (200 mL), washed with brine (200 mL×2). Then the organic phase was dried (Na₂SO₄), filtered and concentrated in vacuo. The residue was purified by column chromatography (PE/EtOAc=10/0~3/1) to give the product as a crude solid which was recrystallized from 2-propanol/n-heptane to give (S,S)-41 (3.03 g, 40% yield) as a solid. The ee of the material at this stage was determined to be above 99%. All spectral data were identical to those of rac-41.

Synthesis of racemic trans-3-(1,3-dibromo-8-oxo-7,8-dihydro-imidazo[1,5-a]pyrazin-6-yl)-4-methyl-pyrrolidine-1-carboxylic acid tert-butyl ester (42)

41

50

Synthesis of racemic trans-3-[1-bromo-3-(3,6-di-hydro-2H-pyran-4-yl)-8-oxo-7,8-dihydro-imidazo[1,5-a]pyrazin-6-yl]-4-methyl-pyrrolidine-1-carboxylic acid tert-butyl ester

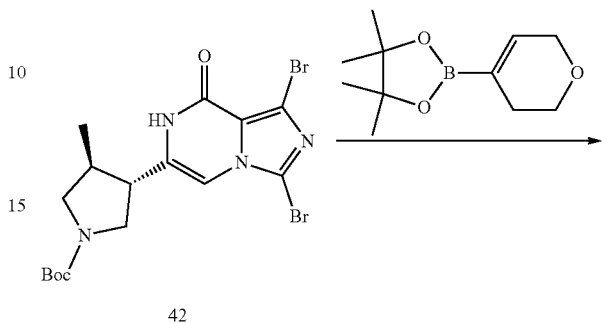

42

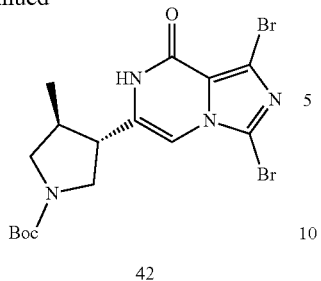

42

To a solution of 41 (3.0 g, 5.89 mmol) in MeOH (150 mL) was added NH₄OAc (9.07 g, 117.8 mmol). The reaction mixture was heated to 130° C. in a pressure vessel for 15 hours. The reaction mixture was filtered and concentrated to get the crude product. The residue was purified by column chromatography (DCM/MeOH=100/1~10/1) to afford racemic trans 42 (2.2 g, 80% yield) as a solid.

¹H NMR (400 MHz, DMSO-d₆): δ 10.98 (br. s, 1H), 7.10 (s, 1H), 3.63-3.54 (m, 2H), 3.39-3.34 (m, 1H), 2.84-2.77 (m, 2H), 2.50 (m, 1H), 1.41 (s, 9H), 0.96 (m, 3H).

Synthesis of (S,S)-trans-3-(1,3-dibromo-8-oxo-7,8-dihydro-imidazo[1,5-a]pyrazin-6-yl)-4-methyl-pyrrolidine-1-carboxylic acid tert-butyl ester (S,S)-(42)

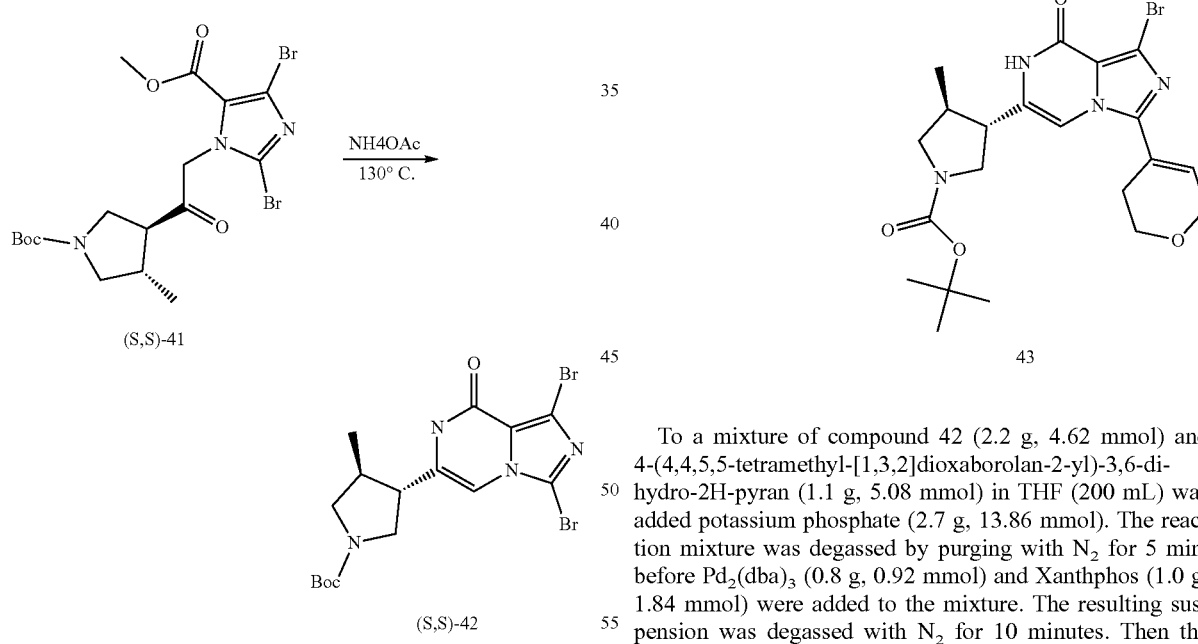

To a solution of (S,S)-41 (3.03 g, 5.9 mmol) in 2-propanol (20 mL) was added NH₄OAc (9.18 g, 118 mmol). The reaction mixture was heated at 105-110° C. for 12 hrs after which it was poured into water (60 mL) with stirring and left for two hrs. The reaction mixture was filtered and concentrated to get the crude product. The residue was purified by column chromatography (DCM/MeOH=100/1~10/1) and evaporated to afford (S,S)-42 (2.1 g, 4.4 mmol) as a solid. The material was determined to have 99.3% ee and similar spectral properties to those of rac-42.

To a mixture of compound 42 (2.2 g, 4.62 mmol) and 4-(4,4,5,5-tetramethyl-[1,3,2]dioxaborolan-2-yl)-3,6-dihydro-2H-pyran (1.1 g, 5.08 mmol) in THF (200 mL) was added potassium phosphate (2.7 g, 13.86 mmol). The reaction mixture was degassed by purging with N₂ for 5 min, before Pd₂(dba)₃ (0.8 g, 0.92 mmol) and Xanthphos (1.0 g, 1.84 mmol) were added to the mixture. The resulting suspension was degassed with N₂ for 10 minutes. Then the mixture reaction was heated to 80° C. under an N₂ atmosphere for 15 hours. After cooling to room temperature, the reaction mixture was diluted with EtOAc (250 mL) and the precipitate was filtered off. The filtrate was concentrated. The crude residue was purified by column chromatography on silica gel (eluting with EtOAc) to afford 43 (1.3 g, 60% yield) as a solid.

¹H NMR (400 MHz, DMSO-d₆): δ 10.80 (m, 1H), 7.34 (s, 1H), 6.42 (s, 1H), 4.30-4.29 (m, 2H), 3.92-3.80 (m, 2H), 3.63-3.33 (m, 4H), 2.87-2.71 (m, 2H), 2.50 (m, 1H), 1.41 (s, 9H), 0.95 (m, 3H).

Synthesis of (S,S)-trans-3-[1-bromo-3-(3,6-dihydro-2H-pyran-4-yl)-8-oxo-7,8-dihydro-imidazo[1,5-a]pyrazin-6-yl]-4-methyl-pyrrolidine-1-carboxylic acid tert-butyl ester (S,S)-(43)

Synthesis of racemic trans-3-methyl-4-[8-oxo-3-(tetrahydro-pyran-4-yl)-7,8-dihydro-imidazo[1,5-a]pyrazin-6-yl]-pyrrolidine-1-carboxylic acid tert-butyl ester (44)

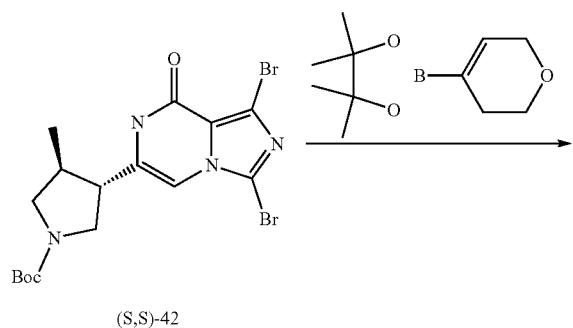

(S,S)-42

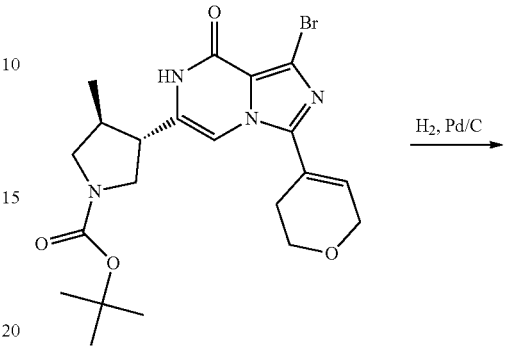

43

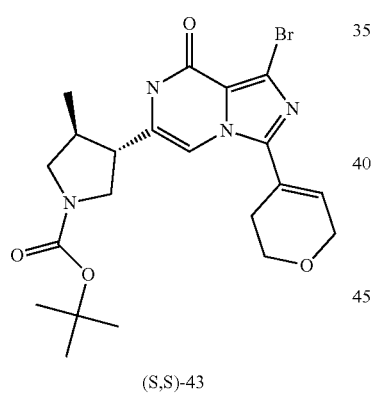

(S,S)-43

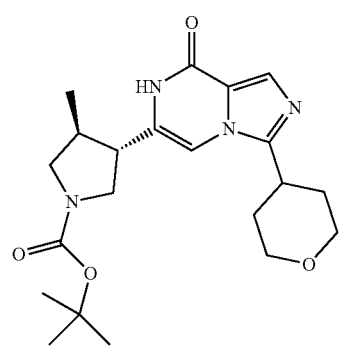

44

To a mixture of compound (S,S)-42 (2.11 g, 4.42 mmol) and 4-(4,4,5,5-tetramethyl-[1,3,2]dioxaborolan-2-yl)-3,6-dihydro-2H-pyran (0.975 g, 4.64 mmol) in 1,4-Dioxane (40 mL) and water (10 mL) was added potassium phosphate (2.57 g, 12.2 mmol). The reaction mixture was degassed by purging with $N_2$ for 5 min, before $Pd_2(dba)_3$ (0.8 g, 0.9 mmol) and Xanthphos (1.0 g, 1.8 mmol) were added to the mixture. The resulting suspension was degassed with $N_2$ for 10 minutes. Then the mixture reaction was heated to 80° C. under an $N_2$ atmosphere for 15 hours. After cooling to room temperature, the reaction mixture was diluted with EtOAc (250 mL) and the solid was removed by filtration through Celite. The filtrate was concentrated. The crude residue was purified by column chromatography on silica gel (eluting with EtOAc) to afford 43 (1.4 g, 2.92 mmol) as a solid. The material has an ee above 99% at this stage.

To a solution of 43 (1.3 g, 2.73 mmol) in DMF (100 mL) and methanol (30 mL) was added 10% Pd/C (0.8 g). The flask was charged with hydrogen (50 psi) and the mixture was stirred at 50° C. overnight. After cooling down, the reaction mixture was filtered through Celite. The filtrate was concentrated under reduced pressure. The crude product was purified by column chromatography on silica gel (eluting with $DCM/CH_3OH=100/1-20/1$) to afford compound 44 (0.99 g, 90% yield) as a solid.

$^1$H NMR (400 MHz, $CDCl_3$): δ 10.80 (br d, 1H), 7.86 (s, 1H), 6.79 (s, 1H), 4.13-4.10 (m, 2H), 3.83-3.79 (m, 3H), 3.63-3.49 (m, 2H), 3.13-3.03 (m, 2H), 2.77-2.75 (m, 2H), 2.54-2.53 (m, 1H), 2.11-2.06 (m, 2H), 1.80-1.85 (m, 2H), 1.48 (m, 9H), 1.12 (d, J=6.4 Hz, 3H).

Synthesis of (S,S)-trans-3-methyl-4-[8-oxo-3-(tetrahydro-pyran-4-yl)-7,8-dihydro-imidazo[1,5-a]pyrazin-6-yl]-pyrrolidine-1-carboxylic acid tert-butyl ester (S,S)-(44)

Synthesis of racemic trans-6-(4-methyl-pyrrolidin-3-yl)-3-(tetrahydro-pyran-4-yl)-7H-imidazo[1,5-a]pyrazin-8-one (45)

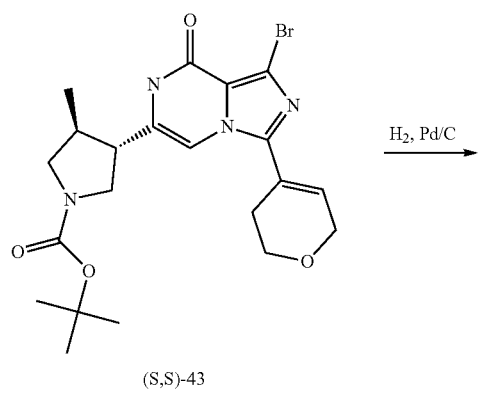

(S,S)-43

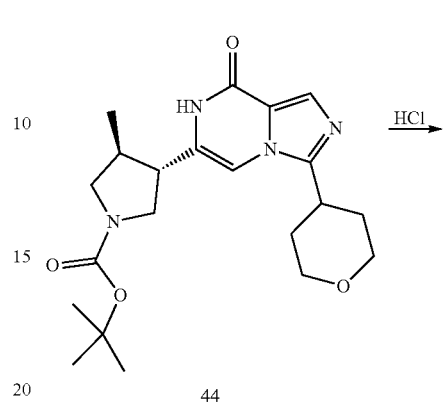

44

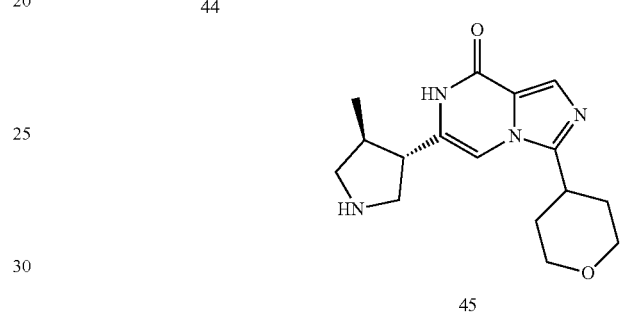

45

To a solution of compound 44 (0.99 g, 2.49 mmol) in CH$_2$Cl$_2$ (20 mL) was added HCl/Et$_2$O solution (20 mL). The resulting mixture was stirred at room temperature for 2 hours. The reaction was concentrated in vacuo to afford racemic trans 45 hydrochloride (0.75 g, 100% yield) as a solid.

$^1$H NMR (400 MHz, DMSO-d$_6$): δ 11.47 (s, 1H), 9.93 (s, 2H), 8.41 (s, 1H), 7.92 (s, 1H), 3.98-3.95 (m, 2H), 3.85-3.80 (m, 1H), 3.58-3.44 (m, 3H), 2.97-2.88 (m, 2H), 2.60-2.50 (m, 3H), 1.98-1.78 (m, 4H), 1.08 (m, 3H).

Synthesis of (S,S)-trans-6-(4-methyl-pyrrolidin-3-yl)-3-(tetrahydro-pyran-4-yl)-7H-imidazo[1,5-a]pyrazin-8-one (S,S)-(45)

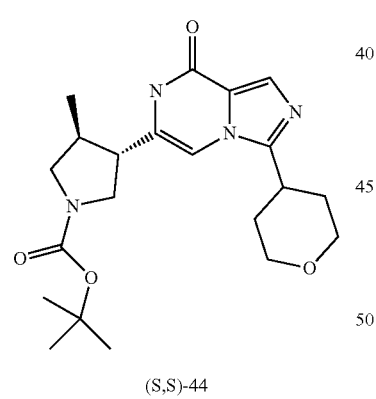

(S,S)-44

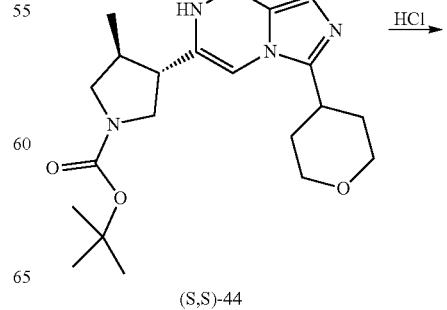

(S,S)-44

A solution of (S,S)-43 (1.15 g, 2.41 mmol) in methanol (50 mL) was placed in an autoclave under N$_2$-protective atmosphere and 10% Pd/C (0.8 g) was added under a nitrogen atmosphere. The reaction mixture was hydrogenated with stirring at 45-50° C. at 10-15 Bar H$_2$ pressure until no more hydrogen was absorbed (24 hrs). After cooling down, the reaction mixture was filtered through Celite. The filtrate was concentrated under reduced pressure. The crude product was purified by column chromatography on silica gel (eluting with DCM/CH$_3$OH=100/1-20/1) to afford compound 44 (0.97 g, 2.41 mmol) as a solid. The ee was determined to be above 99%.

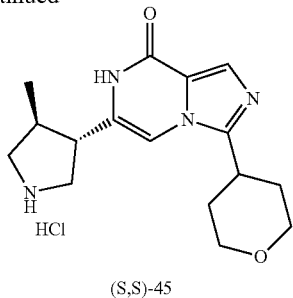

(S,S)-45

To a solution of compound (S,S)-44 (800 mg, 2.0 mmol) was added to a cold (0° C.) solution of HCl in MeOH (1.5 M, 10 mL) and the resulting reaction mixture was stirred while being allowed to reach room temperature. After stirring for 2 hrs the reaction was concentrated in vacuo to afford (S,S)-45 hydrochloride (0.60 g, 2.0 mmol) as a solid.

$^1$H NMR (400 MHz, DMSO-d$_6$): δ 11.47 (s, 1H), 9.93 (s, 2H), 8.41 (s, 1H), 7.92 (s, 1H), 3.98-3.95 (m, 2H), 3.85-3.80 (m, 1H), 3.58-3.44 (m, 3H), 2.97-2.88 (m, 2H), 2.60-2.50 (m, 3H), 1.98-1.78 (m, 4H), 1.08 (m, 3H).

Synthesis of racemic trans-6-(4-methyl-1-pyrimidin-2-ylmethyl-pyrrolidin-3-yl)-3-(tetrahydro-pyran-4-yl)-7H-imidazo[1,5-a]pyrazin-8-one (P3)

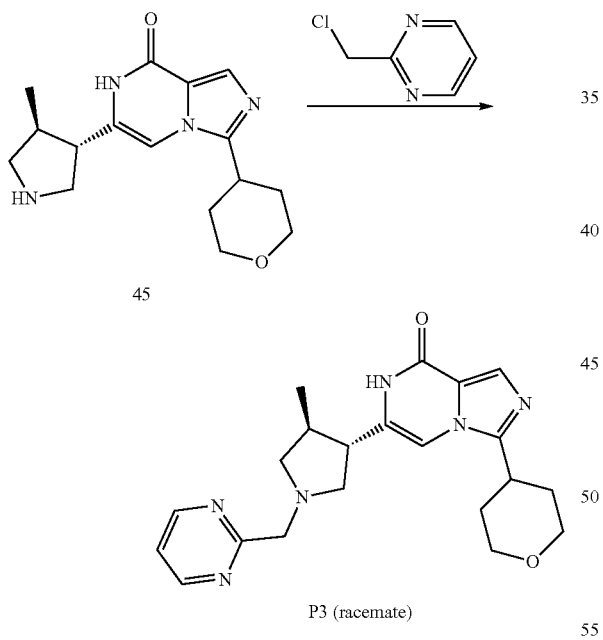

P3 (racemate)

To a solution of compound 45 (0.75 g, 2.49 mmol), 2-chloromethyl-pyrimidine (0.49 g, 2.99 mmol) in DMF (10 mL) and CH$_3$CN (30 mL) was added K$_2$CO$_3$ (1.7 g, 12.5 mmol). The mixture was stirred at 45° C. for 48 hours. The reaction mixture was filtered, concentrated in vacuo. The residue was purified by flash column chromatography (gradient elution from DCM to 15% MeOH in DCM) to afford racemic trans P3 (580 mg, 59% yield) as a solid.

$^1$H NMR (400 MHz, CD$_3$OD): δ 8.85 (d, J=4.8 Hz, 2H), 7.79 (s, 1H), 7.42 (t, J=4.8 Hz, 1H), 7.36 (s, 1H), 4.11-4.04 (m, 3H), 3.93 (d, J=15.2 Hz, 1H), 3.684-3.62 (m, 2H), 3.41-3.32 (m, 2H), 3.16-3.13 (m, 1H), 2.85~2.80 (m, 2H), 2.44-2.40 (m, 1H), 2.28-2.23 (m, 1H), 2.04-1.86 (m, 4H), 1.17 (d, J=6.4 Hz, 3H). MS Calcd.: 394.5; MS Found: 395.8 ([M+H]$^+$).

The racemic mixture of P3 (1.4 g) was separated by Chiral HPLC (Column: Chiralpak IA, 250×4.6 mm×5 um; mobile phase Hex/EtOH/DEA=70:30:0.2) with a flow rate of 1.0 mL/min, to afford P3 enantiomer 1 ((3S,4S)-6-(4-methyl-1-pyrimidin-2-ylmethyl-pyrrolidin-3-yl)-3-(tetrahydro-pyran-4-yl)-7H-imidazo[1,5-a]pyrazin-8-one, or 6-[(3S,4S)-4-methyl-1-(pyrimidin-2-ylmethyl)pyrrolidin-3-yl]-3-tetrahydropyran-4-yl-7H-imidazo[1,5-a]pyrazin-8-one) (0.52 g, RT=9.98 min) and P3 enantiomer 2 ((3R,4R)-6-(4-methyl-1-pyrimidin-2-ylmethyl-pyrrolidin-3-yl)-3-(tetrahydro-pyran-4-yl)-7H-imidazo[1,5-a]pyrazin-8-one opposite of P3 enantiomer 1) (0.49 g, RT=12.6 min).

Synthesis of (S,S)-trans-6-(4-methyl-1-pyrimidin-2-ylmethyl-pyrrolidin-3-yl)-3-(tetrahydro-pyran-4-yl)-7H-imidazo[1,5-a]pyrazin-8-one (S,S)-(P3)

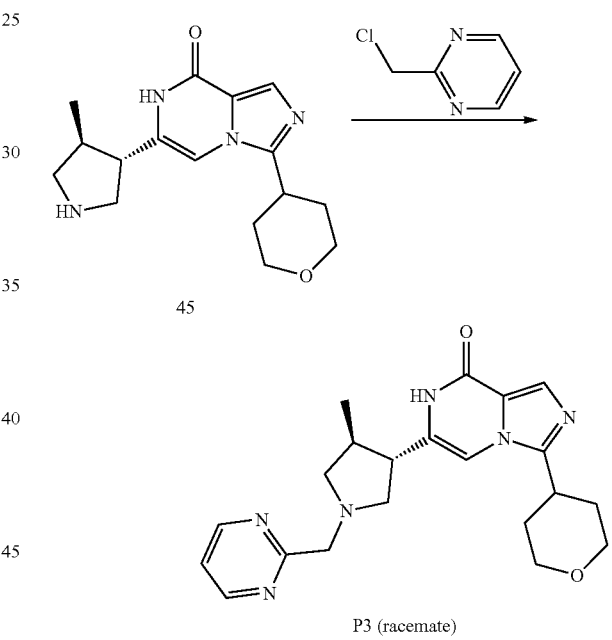

P3 (racemate)

To a solution of compound (S,S)-45 (0.60 g, 2.0 mmol) and 2-chloromethyl-pyrimidine (0.40 g, 2.40 mmol) in DCM (15 mL) was added DIPEA (3.1 g, 24 mmol) and the mixture was stirred at RT for 24 hrs (at this time all the starting material had been converted). The reaction mixture was cooled to 5° C., and deionised water (10 mL) was added. The pH of the aqueous phase was adjusted to pH 6.0 with addition of conc hydrochloric acid (about 1 mL) while keeping the temperature of the mixture <25° C. The phases were allowed to separate and the organic phase was washed with brine (3×5 mL) (these washings were discarded). The aqueous phase was extracted with dichloromethane (10 mL), and the organic phase from this extraction was washed with brine (3×5 mL). The combined organic phases were dried over sodium sulfate (3 g) for 1 hour, filtered and evaporated. The resulting residue was subjected to column chromatography (as described for rac-(P3)) to give (S,S)-P3 (580 mg, 59% yield) as a solid after evaporation. This material has ee above 99% and is identical in all ways to P3 Enantiomer 1 (described above).

Synthesis of (aminooxy) (diphenyl) phosphine oxide (B)

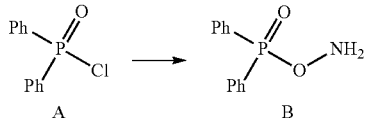

To a suspension of hydroxylamine hydrochloride (73.5 g, 1.05 mol) in dichloromethane (500 mL) was added DIPEA (136 g, 1.05 mol) over 15 minutes at −30° C. under a nitrogen atmosphere. A white precipitate formed upon the addition. After stirring for one hour at that temperature, a solution of diphenylphosphinic chloride A (50 g, 0.2 mol) in dichloromethane (100 mL) was added over 60 minutes. The mixture reaction was warmed to 0° C. over 1 hour with stirring. The reaction was quenched by adding water (200 mL) over 10 minutes. After stirring the mixture for 0.5 hour, the precipitate was collected by filtration and washed with water (100 mL×2). Then the solid was dried under reduced pressure to afford a crude product. The crude product was triturated in EtOH to afford compound B (27 g, 56% yield) as a white solid.

¹HNMR (400 MHz, CD₃OD): δ77.91-7.79 (m, 5H), 7.62-7.50 (m, 7H).

MS Calcd.: 233; MS Found: 234 ([M+H]⁺).

Synthesis of 3-amino-3H-imidazole-4-carboxylic acid methyl ester (46)

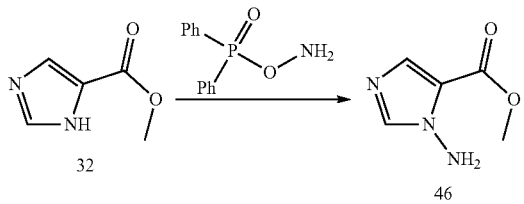

To a solution of compound 3H-Imidazole-4-carboxylic acid methyl ester 32 (30.0 g, 0.24 mol) in THF (1.0 L) was dropwise added LiHMDS (239 mL, 10M in THF, 2.4 mol) over 2 hours at −78° C. Then the reaction mixture was stirred at −78° C. for another two hours and allowed to warm to −10° C. Compound B (60.0 g, 0.26 mol) was added at this temperature. Then the mixture reaction was stirred at ambient temperature overnight. After quenching with water (250 mL), the reaction mixture was concentrated. The crude product was purified by column chromatography on silica gel (DCM/MeOH=20/1) to afford compound 46 (24 g, 73% yield) as a solid.

¹H NMR (400 MHz, DMSO-d6): δ 7.82 (s, 1H), 7.51 (s, 1H), 6.20 (s, 2H), 3.79 (s, 3H). MS Calcd.: 382; MS Found: 383 ([M+H]⁺). MS Calcd.: 141; MS Found: 142 ([M+H]⁺).

Synthesis of 3-(2-benzyloxy-acetylamino)-3H-imidazole-4-carboxylic acid methyl ester (47)

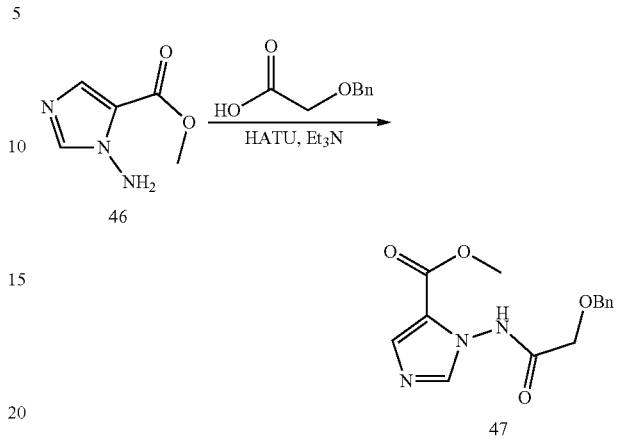

To a solution of compound 46 (4.9 g, 30 mmol), benzyloxy-acetic acid (5.8 g, 30 mmol) and DIPEA (18.6 ml, 90 mmol) in DMF (100 mL) was added HATU (15.8 g, 36 mmol) whilst cooling on an ice-water bath. The mixture was then stirred at t ambient temperature overnight. After removal of the solvent, the residue was purified by chromatography on a silica gel column (eluted with PE/EtOAc=10:1 to 2:1) to afford compound 47 (6.1 g, 61% yield) as an oil.

¹H NMR (400 MHz, CDCl₃): δ 9.93 (br. s, 1H), 7.74 (s, 1H), 7.67 (s, 1H), 7.39-7.33 (m, 5H), 4.70 (s, 2H), 4.23 (s, 2H), 3.83 (s, 3H). MS Calcd.: 289; MS Found: 300 ([M+H]⁺).

Synthesis of 3-(2-benzyloxy-acetylamino)-3H-imidazole-4-carboxylic acid amide (48)

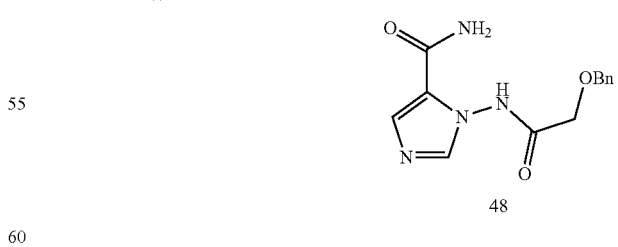

Compound 47 (30.0 g, 100 mmol) and conc aq. ammonia (300 mL) were combined in a sealed tube and heated to 70° C. under microwave radiation for 2 hours. The resulting mixture was concentrated in vacuo to afford compound 48 (26.3 g, 96% yield) as a solid. MS Calcd.: 274; MS Found: 275 ([M+H]⁺).

Synthesis of 2-benzyloxymethyl-3H-imidazo[5,1-f][1,2,4]triazin-4-one (49)

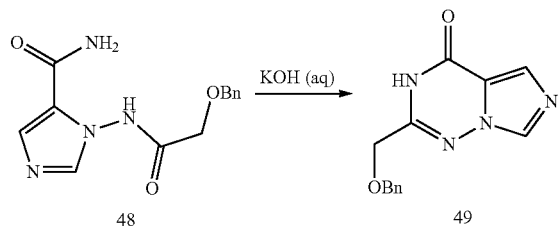 [SMILES: NC(=O)c1cncn1NC(=O)COCc1ccccc1 ; O=c1[nH]c(COCc2ccccc2)nn2cncc12]

To a solution of compound 48 (28.0 g, 100 mmol) in EtOH (240 mL) was dropwise added a solution of KOH (19.8 g, 300 mmol) in water (200 mL). The resulting solution was heated to reflux for 3 hours. After removal of the organic solvent in vacuo, the mixture was poured into ice water and the pH was adjusted to 7.0 with 1M aq HCl solution. The suspension was filtered off and dried to afford compound 49 (11.3 g, 44.1% yield) as a solid.

$^1$H NMR (400 MHz, DMSO-d6): δ 12.05 (s, 1H), 8.45 (s, 1H), 7.74 (s, 1H), 7.39-7.29 (m, 5H), 4.59 (s, 2H), 4.36 (s, 2H). MS Calcd.: 256; MS Found: 257 ([M+H]$^+$).

Synthesis of 2-benzyloxymethyl-7-iodo-3H-imidazo[5,1-f][1,2,4]triazin-4-one (50)

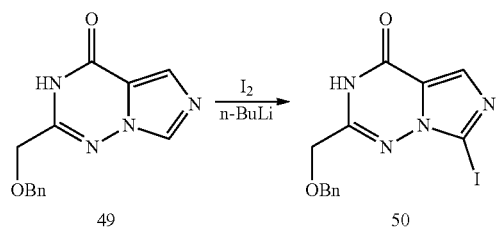

To a solution of compound 49 (10.0 g, 38.2 mmol) in THF (240 mL) was dropwise added n-BuLi (46 mL) at −78° C. and the reaction was stirred below −70° C. for one hour. Iodine (39.3 g, 153 mol) in THF (120 mL) was added dropwise at this temperature and then the reaction temperature was allowed to warm to room temperature slowly. The reaction was quenched with saturated Na$_2$SO$_3$ aqueous solution (120 mL), and then extracted with EtOAc (150 mL×3). The combined organic phases were dried over Na$_2$SO$_4$, filtered and concentrated in vacuo to get the crude product. The residue was purified by chromatography on silica gel column (eluted with PE/EtOAc=10:1 to 2:1) to afford compound 50 (4.75 g, 32.5% yield) as a solid.

$^1$H NMR (400 MHz, DMSO-d6): δ 12.16 (br. s, 1H), 7.84 (s, 1H), 7.42-7.29 (m, 5H), 4.62 (s, 2H), 4.40 (s, 2H). MS Calcd.: 382; MS Found: 383 ([M+H]$^+$).

Synthesis of 2-benzyloxymethyl-7-(3,6-dihydro-2H-pyran-4-yl)-3H-imidazo[5,1-f][1,2,4]triazin-4-one (51)

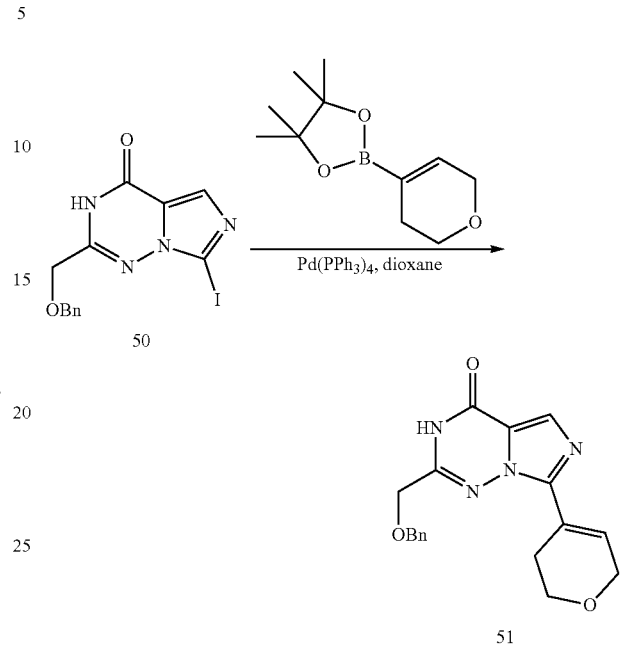

To a solution of compound 50 (4.75 g, 10.0 mmol) in dioxane (80 mL) was dropwise added a solution of Cs$_2$CO$_3$ (9.88 g, 30 mmol) in water (12 mL), followed by Pd(PPh$_3$)$_4$ (2.36 g, 2.00 mmol) and 4-(4,4,5,5-tetramethyl-[1,3,2]dioxaborolan-2-yl)-3,6-dihydro-2H-pyran (3.86 g, 18.0 mmol). The reaction mixture was degassed by purging with N$_2$ for 15 min. Then the mixture was heated to reflux for 16 hours. After removal of the solvent in vacuo, the residue was purified by chromatography on a silica gel column (eluted with PE/EtOAc=10:1 to 1:5) to afford compound 51 (2.1 mg, 76% yield) as a solid.

$^1$H NMR (400 MHz, DMSO-d6): δ 12.10 (br. s, 1H), 7.78 (s, 1H), 7.39-7.30 (m, 5H), 7.25 (s, 1H), 4.62 (s, 2H), 4.41 (s, 2H), 4.27 (d, J=2.8 Hz, 2H), 3.82 (t, J=5.2 Hz, 2H), 2.63 (m, 2H). MS Calcd.: 338; MS Found: 339 ([M+H]$^+$).

Synthesis of 2-hydroxymethyl-7-(tetrahydro-pyran-4-yl)-3H-imidazo[5,1-f][1,2,4]triazin-4-one (52)

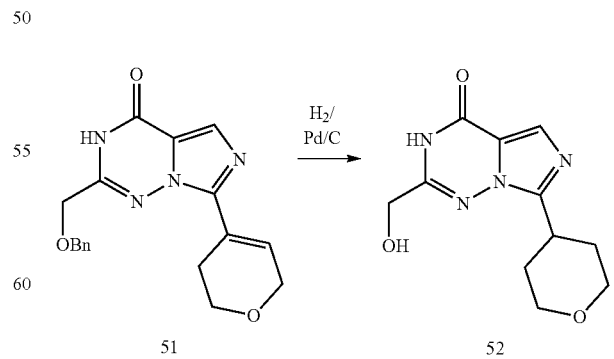

To a solution of compound 51 (1.8 g, 5.0 mmol) in MeOH (70 mL) was added Pd(OH)$_2$ (20% on Carbon (wetted with ca. 50% Water), 400 mg). The reaction flask was charged with hydrogen (50 psi) and the mixture was stirred on an oil bath heated to 70° C. until LC/MS showed that the starting material had been consumed. The suspension was filtered through celite, the filter was washed with MeOH (100 mL×2) and the combined organic phases were concentrated in vacuo to afford compound 52 (1.0 g, 79% yield) as a solid.

$^1$H NMR (400 MHz, DMSO-d6): δ 11.65 (s, 1H), 7.68 (s, 1H), 4.30 (s, 2H), 3.96-3.92 (m, 2H), 3.51-3.17 (m, 3H), 1.88-1.81 (m, 4H). MS Calcd.: 250; MS Found: 251 ([M+H]$^+$).

Synthesis of 2-chloromethyl-7-(tetrahydropyran-4-yl)-3H-imidazo[5,1-f][1,2,4]triazin-4-one (53)

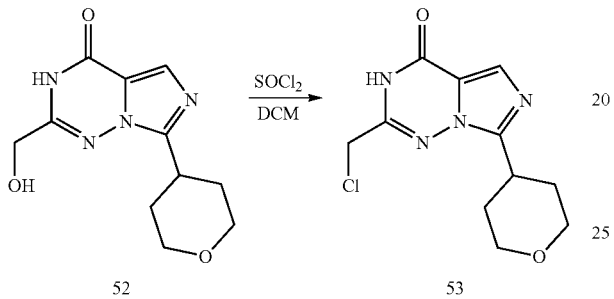

To a solution of compound 52 (1.0 g, 4 mmol) in CH$_2$Cl$_2$ (50 mL) was dropwise added SOCl$_2$ (15 mL) whilst cooling on an ice-water bath. The resulting mixture was then stirred at ambient temperature overnight. The reaction mixture was concentrated in vacuo to afford compound 53 (1.07 g, 100% yield) as a solid.

$^1$H NMR (400 MHz, DMSO-d6): δ 12.50 (br. s, 1H), 8.02 (s, 1H), 4.57 (s, 2H), 3.95 (m, 2 H), 3.57-3.48 (m, 3H), 1.91-1.81 (m, 4H). MS Calcd.: 268; MS Found: 269 ([M+H]$^+$).

Synthesis of 3-(4-fluoro-benzyloxy)-azetidine-1-carboxylic acid tert-butyl ester (2)

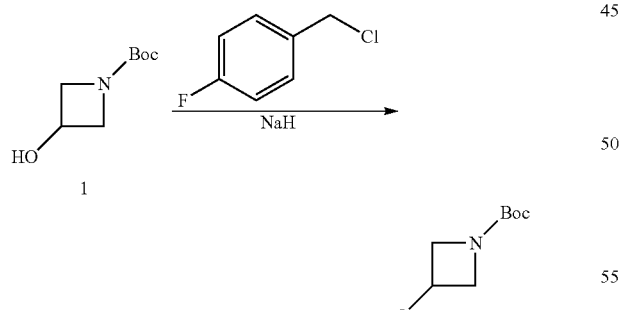

To a solution of compound 3-hydroxy-azetidine-1-carboxylic acid tert-butyl ester 1 (5.30 g, 30 mmol) in DMF (60 mL) was added NaH (1.80 g, 45 mmol) whilst cooling on an ice-water bath. The suspension was then stirred at this temperature for one hour, followed by the addition of 1-chloromethyl-4-fluoro-benzene (8.94 g, 60 mmol). The resulting mixture was stirred at ambient temperature overnight. The reaction mixture was poured into water (200 mL) and extracted with EtOAc (150 mL×3). The organic combined phases were dried over Na$_2$SO$_4$, filtered and concentrated in vacuo to get the crude product. The residue was purified by chromatography on a silica gel column (eluted with PE/EtOAc=10:1 to 2:1) to afford compound 2 (7.90 g, 94% yield) as an oil.

$^1$H NMR (300 MHz, DMSO-d6): δ 7.41-7.37 (m, 2H), 7.21-7.14 (m, 2H), 4.40 (s, 2H), 4.33-4.29 (m, 1H), 4.02-3.97 (m, 2H), 3.68-3.66 (m, 2H), 1.37 (s, 9H). MS Calcd.: 281; MS Found: 282 ([M+H]$^+$).

Synthesis of 3-(4-fluoro-benzyloxy)-azetidine (3)

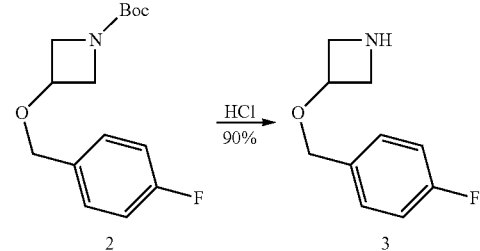 [SMILES: CC(C)(C)OC(=O)N1CC(OCc2ccc(F)cc2)C1 ; Cl ; Fc1ccc(COC2CNC2)cc1]

To a solution of compound 2 (2.68 g, 9.30 mmol) in dioxane (30 mL) was added HCl/dioxane (4 M, 9.25 mL) under ice-water bath. The reaction mixture was then stirred at ambient temperature overnight. The reaction solution was concentrated in vacuo to afford compound 3 hydrochloride (1.2 g, 71% yield) as a solid.

$^1$H NMR (300 MHz, DMSO-d6): δ 7.36 (m, 2 H), 7.16 (m, 2 H), 4.35 (s, 2H), 4.39 (m, 1 H), 3.47 (t, J=7.5 Hz, 2 H), 3.38 (t, J=7.2 Hz, 2 H). MS Calcd.: 181; MS Found: 182 ([M+H]$^+$).

Synthesis of 2-[3-(4-fluoro-phenoxy)-azetidin-1-ylmethyl]-7-(tetrahydro-pyran-4-yl)-3H-imidazo[5,1-f][1,2,4]triazin-4-one (P4)

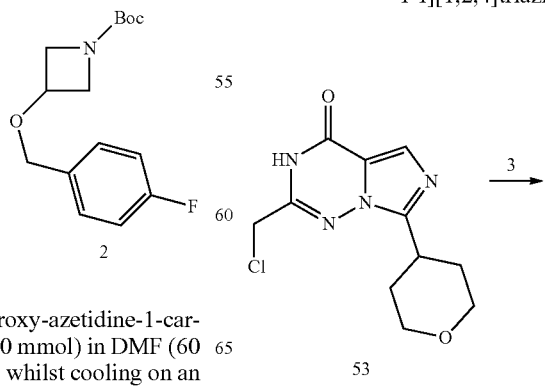

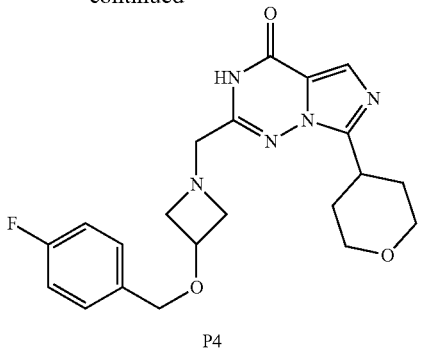

P4

To a solution of compound 53 (1.27 mg, 4.0 mmol) and compound 3 (1.8 g, 8.3 mmol) in $CH_3CN$ (20 mL) was added DIPEA (2.61 mL, 20 mmol). The result solution was heated to 70° C. for 2 hours. TLC indicated that the reaction was complete. The reaction was concentrated in vacuum. The residue was purified by column chromatography on silica gel (eluted with DCM/MeOH 100:1 to 30:1) to afford the desired product P4 (1.23 g, 74% yield) as a solid.

$^1$H NMR (400 MHz, DMSO-d6): δ 11.70 (br. s, 1H), 7.67 (s, 1 H), 7.37 (m, 2 H), 7.16 (m, 2H), 4.38 (s, 2H), 4.17 (m, 1H), 3.95~3.92 (m, 2H), 3.56 (t, J=8.0 Hz, 2H), 3.54~3.46 (m, 4H), 3.37~3.35 (m, 1H), 3.06~3.03 (m, 2H), 1.86~1.80 (m, 4H). MS Calcd.: 413; MS Found: 414 ([M+H]$^+$).

Example 2

X-Ray Crystal Structure of P3 Enantiomer 2

The single crystal X-ray structure of P3 enantiomer 2 has been determined at 100 K in the orthorhombic system, space group $P2_12_12_1$ using a crystal grown. There is one compound molecule and one molecule of water in the asymmetric unit. The final R1 [I>2δ(I)]=3.09%. The absolute stereochemistry of the compound has been FIG. 1.

P3 Enantiomer 2 Monohydrate
Instrument and Methodology Details
Crystallisation experiments were conducted to obtain suitable crystals to determine the structure and absolute configuration of P3 enantiomer 2 by single crystal X-ray diffraction.
X-Ray Powder Diffraction (XRPD)
X-Ray Powder Diffraction patterns were collected on a Bruker D8 diffractometer using Cu Kα radiation (40 kV, 40 mA), θ-2 θ goniometer, and divergence of V4 and receiving slits, a Ge monochromate and a Lynxeye detector. The instrument is performance checked using a certified Corundum standard (NIST 1976). The software used for data collection was Diffrac Plus XRD Commander v2.6.1 and the data were analysed and presented using Diffrac Plus EVA v15.0.0.0.

Samples were run under ambient conditions as flat plate specimens using powder as received. The sample was gently packed into a cavity cut into polished, zero-background (510) silicon wafer. The sample was rotated in its own plane during analysis. The details of the data collection are: Angular range: 2 to 42° 2θ; Step size: 0.05° 2 θ; Collection time: 0.5 s/step.
Single Crystal X-Ray Diffraction (SCXRD)
Data were collected on an Oxford Diffraction Supernova Dual Source, Cu at Zero, Atlas CCD diffractometer equipped with an Oxford Cryosystems Cobra cooling device. The data were collected using CuKα radiation. Structures were typically solved using either the SHELXS or SHELXD programs and refined with the SHELXL program as part of the Bruker AXS SHELXTL suite (V6.10). Unless otherwise stated, hydrogen atoms attached to carbon were placed geometrically and allowed to refine with a riding isotropic displacement parameter. Hydrogen atoms attached to a heteroatom were located in a difference Fourier synthesis and were allowed to refine freely with an isotropic displacement parameter.
Polarised Light Microscopy (PLM)
Samples were studied on a Nikon SMZ 1500 polarized light microscope with a digital video camera connected to a DS Camera control unit DS-L2 for image capture. A small amount of each sample was placed on a glass slide, mounted in immersion oil, the individual particles being separated as well as possible. The sample was viewed with appropriate magnification and partially polarized light, coupled to a λ false-colour filter.
Crystallisation Screen
Dissolution of P3 enantiomer 2 (5 mg) was attempted in selected solvent systems at 50° C. The solutions were placed in the fridge at 4° C. for 48 hours. The suspensions were filtered, and the resulting mother liquors were also placed at 4° C. Any cyrstals obtained were assessed by optical microscopy.

The material was soluble in most of solvent systems assessed, with the exception of isopropyl acetate and cumene. Large prism shaped crystals were obtained at 4° C. from a range of solvents, including acetonitrile, tetrahydrofurane and 1,4-dioxane. The crystal structure of P3 enantiomer 2 was solved using crystals obtained by cooling in acetonitrile.
Single Crystal Structure Determination
A crystalline sample of P3 enantiomer 2 was obtained by dissolving 5 mg of the supplied material in 50 μl of acetonitrile and cooling at 4° C. The crystals as obtained were of prism morphology. A crystal of sufficient size and quality for analysis by single crystal X-ray diffraction was isolated with approximate dimensions 0.25×0.15×0.11 mm. Optical micrographs of the crystals as received and the single crystal used for the data collection are shown in FIG. 1.

Figure 3:
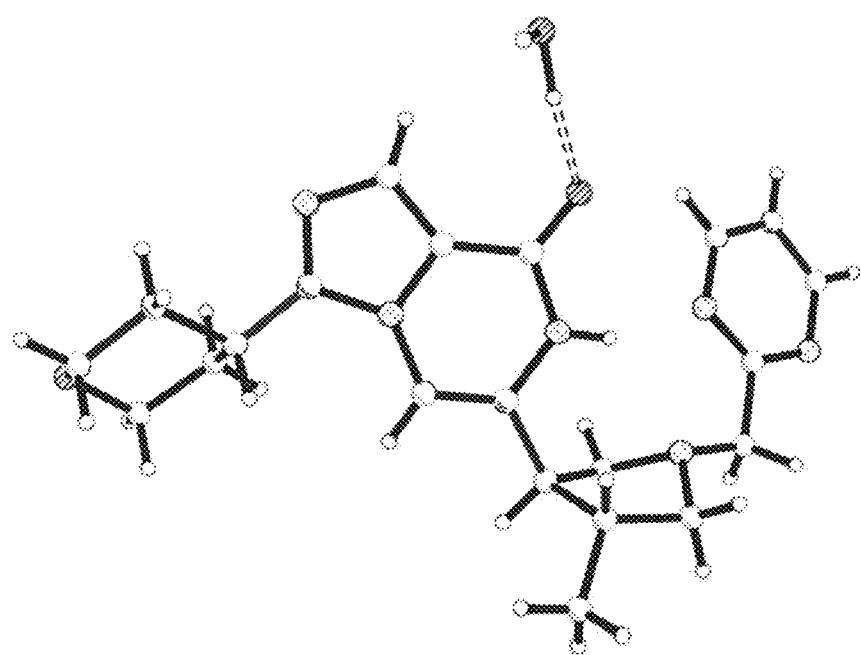
FIG. 3 is a ball and stick diagram of Compound P3 enantiomer 2 monohydrate.

The structure was determined at 100 K in the orthorhombic system, space group $P2_12_12_1$ with the final R1 {I>2δ(I)]=3.09%. The compound was identified as a monohydrate of P3 enantiomer 2 as depicted in FIG. 1 and FIG. 3. The asymmetric unit contains a fully ordered molecule of P3 enantiomer 2 and one molecule of water. Anisotropic atomic displacement ellipsoids for the non-hydrogen atoms are shown at the 50% probability level. Hydrogen atoms are displayed with an arbitrarily small radius.

For the absolute stereochemistry of P3 enantiomer 2 shown in FIG. 1, C12 and C13 (the numbering is not the numbers used in IUPAC names) are in the R configuration, the Flack parameter=−0.03 (4). For the inverted structure with C12 and C13 in the S configuration (P3 enantiomer 1), the Flack parameter=1.03 (4).

Determination of the absolute structure using Bayesian statistics on Bijvoet differences, reveals that the probability of the absolute structure as presented being correct is 1.000, while the probabilities of the absolute structure being a racemic twin or false are both 0.000. The Flack equivalent and its uncertainty are calculated through this program to be −0.02 (4). The calculation was based on 1806 Bijvoet pairs with a coverage of 100%.

Conformational analysis of P3 enantiomer 2 shows the pyrimidine ring is planar, the pyrrolidine ring is an envelope on the nitrogen, and the tetrahydropyran ring is a chair.

As the opposite of P3 enantiomer 2, P3 enantiomer 1 has a structure of:

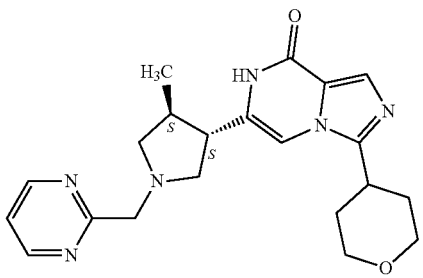

Example 3

In Vitro Testing

PDE9 Inhibition Assay

A PDE9 assay may for example, be performed as follows: The assay is performed in 60 uL samples containing a fixed amount of the relevant PDE enzyme (sufficient to convert 20-25% of the cyclic nucleotide substrate), a buffer (50 mM HEPES7.6; 10 mM $MgCl_2$; 0.02% Tween20), 0.1 mg/ml BSA, 225 pCi of $^3$H-labelled cyclic nucleotide substrate, tritium labeled cAMP to a final concentration of 5 nM and varying amounts of inhibitors. Reactions are initiated by addition of the cyclic nucleotide substrate, and reactions are allowed to proceed for one hr at room temperature before being terminated through mixing with 15 uL 8 mg/mL yttrium silicate SPA beads (Amersham). The beads are allowed to settle for one hr in the dark before the plates are counted in a Wallac 1450 Microbeta counter. The measured signal can be converted to activity relative to an uninhibited control (100%) and $IC_{50}$ values can be calculated using the Xlfit extension to EXCEL.

In the context of the present invention the assay was performed in 60 uL assay buffer (50 mM HEPES pH 7.6; 10 mM $MgCl_2$; 0.02% Tween20) containing enough PDE9 to convert 20-25% of 10 nM $^3$H-cAMP and varying amounts of inhibitors. Following a 1 hour incubation the reactions were terminated by addition of 15 uL 8 mg/mL yttrium silicate SPA beads (Amersham). The beads were allowed to settle for one hr in the dark before the plates were counted in a Wallac 1450 Microbeta counter. $IC_{50}$ values were calculated by nonlinear regression using XLfit (IDBS).

Results of the experiments showed that the tested compounds of the invention inhibit the PDE9 enzyme with $IC_{50}$ values below 100 nM.

PDE1 Inhibition Assay

PDE1 assays were performed as follows: the assays was performed in 60 μL samples containing a fixed amount of the PDE1 enzym1 (sufficient to convert 20-25% of the cyclic nucleotide substrate), a buffer (50 mM HEPES pH 7.6; 10 mM $MgCl_2$; 0.02% Tween20), 0.1 mg/ml BSA, 15 nM tritium labelled cAMP and varying amounts of inhibitors. Reactions were initiated by addition of the cyclic nucleotide substrate, and reactions were allowed to proceed for 1 h at room temperature before being terminated through mixing with 20 μL (0.2 mg) yttrium silicate SPA beads (PerkinElmer). The beads were allowed to settle for 1 h in the dark before the plates were counted in a Wallac 1450 Microbeta counter.

The measured signals were converted to activity relative to an uninhibited control (100%) and $IC_{50}$ values were calculated using XlFit (model 205, IDBS).

Example 4

In Vivo Testing

Blood Brain Barrier Penetration

Male CD mice (20-24 g) were housed pair-wise with free access to food and water for an acclimatization period of 3-7 days before initiation of experiments. Prior to dosing the animals were fasted overnight. During testing, mice were kept in individual cages. The brain-to-plasma distribution was assessed 30 minutes and 2 hours after subcutaneous administration of the test compound at a dose of 10 mg/kg (n=3 at each time point). The dose volume was 10 ml/kg using appropriate vehicle to solubilize each test compound. At the time of sampling, animals were anesthetized with isoflurane and a systemic blood sample collected by cardiac puncture into vacutainers containing sodium heparin as anti-coagulant. The blood was centrifuged at 3500 rpm for 10 minutes at 4° C. to obtain plasma. Following decapitation, brains were dissected out and transferred to pre-weighed vessels followed by tissue weights determination. Plasma and brains were stored at −80° C. until quantitative bioanalysis by LC-MS/MS. Results are expressed as ng/ml for plasma and ng/g for brain samples.

The invention claimed is:

1. A compound that is (3S,4S)-6-(4-methyl-1-pyrimidin-2-ylmethyl-pyrrolidin-3-yl)-3-(tetrahydro-pyran-4-yl)-7H-imidazo[1,5-a]pyrazin-8-one.

2. A pharmaceutical composition comprising a therapeutically effective amount of the compound in claim 1, and one or more pharmaceutically acceptable carriers, diluents or excipients.

3. A method of treating a subject suffering from benign prostate hyperplasia or sickle cell disease comprising administering the pharmaceutical composition of claim 2 to the subject in need thereof.

4. A method of treating a subject suffering from benign prostate hyperplasia or sickle cell disease comprising administering a therapeutically effective amount of the compound in claim 1 to the subject in need thereof.

* * * * *